US012740803B2

(12) United States Patent
Zhang

(10) Patent No.: US 12,740,803 B2
(45) Date of Patent: Sep. 22, 2026

(54) ULTRASONIC SCALPEL HANDLE, ULTRASONIC SCALPEL AND ULTRASONIC SCALPEL SYSTEM

(71) Applicant: Ensurge Medical (Suzhou) Co., Ltd., Suzhou (CN)

(72) Inventor: Jun Zhang, Suzhou (CN)

(73) Assignee: Ensurge Medical (Suzhou) Co., Ltd., Suzhou (CN)

( * ) Notice: Subject to any disclaimer, the term of this patent is extended or adjusted under 35 U.S.C. 154(b) by 698 days.

(21) Appl. No.: 18/251,391

(22) PCT Filed: Oct. 22, 2021

(86) PCT No.: PCT/CN2021/125632
§ 371 (c)(1),
(2) Date: Oct. 16, 2023

(87) PCT Pub. No.: WO2022/095728
PCT Pub. Date: May 12, 2022

(65) Prior Publication Data

US 2025/0339169 A1 Nov. 6, 2025

(30) Foreign Application Priority Data

Nov. 4, 2020 (CN) ......................... 202011212999.8
Mar. 3, 2021 (CN) ......................... 202120458579.1
Jun. 28, 2021 (CN) ......................... 202110721818.2

(51) Int. Cl.
*A61B 17/3213* (2006.01)
*A61B 17/00* (2006.01)
*A61B 17/32* (2006.01)

(52) U.S. Cl.
CPC .. *A61B 17/3213* (2013.01); *A61B 17/320092* (2013.01); *A61B 2017/00367* (2013.01);
(Continued)

(58) Field of Classification Search
CPC .... A61B 17/320068; A61B 17/320092; A61B 17/3213; A61B 2017/00367;
(Continued)

(56) References Cited

U.S. PATENT DOCUMENTS 6,129,392 A 10/2000 Dittrich et al.
6,386,789 B1 5/2002 Chausse et al.
(Continued)

FOREIGN PATENT DOCUMENTS

CN 104783868 A * 7/2015 ......... A61B 17/3213
CN 105939679 A 9/2016
(Continued)

OTHER PUBLICATIONS

Chinese Office Action issued for Chinese Patent Application No. 202110721818.2, dated Dec. 24, 2021 in 14 pages including English translation.

(Continued)

*Primary Examiner* — Robert A Lynch
(74) *Attorney, Agent, or Firm* — Knobbe, Martens, Olson & Bear, LLP

(57) ABSTRACT

An ultrasonic scalpel handle, an ultrasonic scalpel and an ultrasonic scalpel system, wherein the ultrasonic scalpel comprises the ultrasonic scalpel handle and cutting tool. The cutting tool comprises an inner tube, an outer tube and a tool bar which extend in the front-rear direction, wherein the tool bar is disposed through the inner tube and the outer tube is sleeved outside the inner tube. The ultrasonic scalpel handle comprises a handle housing and a transducer assembly. The transducer assembly at least comprises a transducer having a horn shaft which extends in the front-rear direction. A novel connection assembly is disposed inside the ultrasonic scalpel handle and achieves stable and reliable connection between the cutting tool and the ultrasonic scalpel handle.

(Continued)

Thus the cutting tool is easy to mount and operate, does not shake during a surgery operation, has better operation accuracy.

34 Claims, 10 Drawing Sheets

(52) U.S. Cl.
CPC ................. *A61B 2017/0042* (2013.01); *A61B 2017/0046* (2013.01); *A61B 2017/320075* (2017.08); *A61B 2017/320082* (2017.08); *A61B 2017/320093* (2017.08)

(58) Field of Classification Search
CPC .... A61B 2017/0042; A61B 2017/0046; A61B 2017/0047; A61B 2017/2929; A61B 2017/320075; A61B 2017/320082; A61B 2017/320093
See application file for complete search history.

(56) References Cited

U.S. PATENT DOCUMENTS

| | | | |
|---|---|---|---|
| 6,623,500 | B1 | 9/2003 | Cook et al. |
| 8,852,208 | B2 | 10/2014 | Gomez et al. |
| 2011/0077621 | A1 | 3/2011 | Graham et al. |
| 2012/0221030 | A1 | 8/2012 | Yamada |
| 2015/0051516 | A1 | 2/2015 | Sanai et al. |
| 2015/0073457 | A1 | 3/2015 | Stoddard et al. |
| 2019/0008546 | A1 | 1/2019 | Ruiz Ortiz et al. |

FOREIGN PATENT DOCUMENTS

| | | | |
|---|---|---|---|
| CN | 107280735 | A | 10/2017 |
| CN | 109171888 | A | 1/2019 |
| CN | 110099647 | A | 8/2019 |
| CN | 209404883 | U | 9/2019 |
| CN | 112237465 | A | 1/2021 |
| CN | 113349889 | A | 9/2021 |
| JP | 2002-177295 | A | 6/2002 |
| JP | 2009-195676 | A | 9/2009 |
| JP | 5933874 | B1 | 6/2016 |
| JP | 2020-527969 | A | 9/2020 |
| JP | 7539120 | B2 | 8/2024 |
| KR | 10-2020-0096602 | A | 8/2020 |
| RU | 78724 | U1 | 12/2008 |
| RU | 168974 | U1 | 2/2017 |
| WO | WO 2008/017909 | A1 | 2/2008 |

OTHER PUBLICATIONS

International Search Report and Written Opinion issue in the International Patent Application No. PCT/CN2021/125632, dated Jan. 18, 2022 in 13 pages.

* cited by examiner

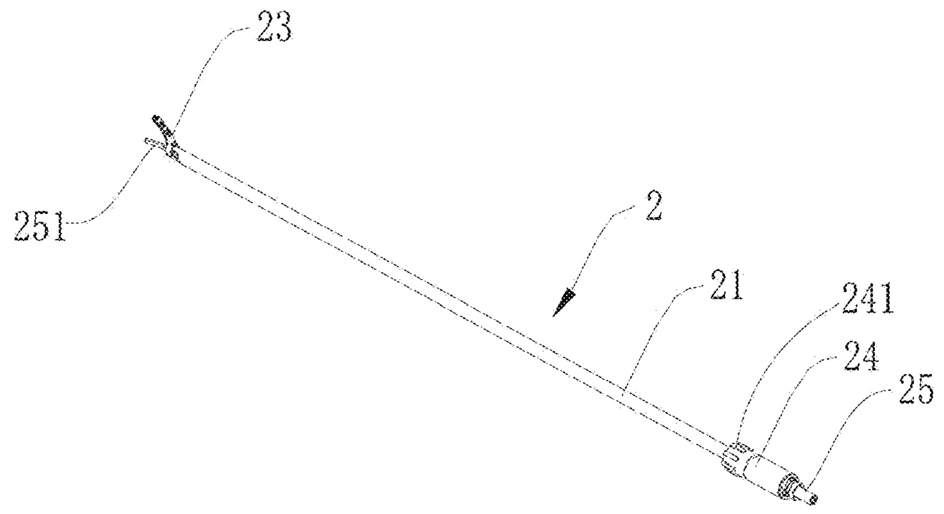
Figure 4
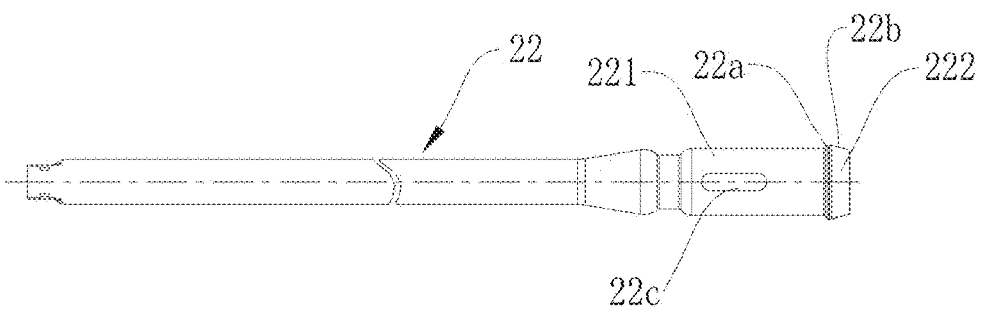
Figure 5
2
171
152
151
142
143
161
144
145
161
141
Figure 6

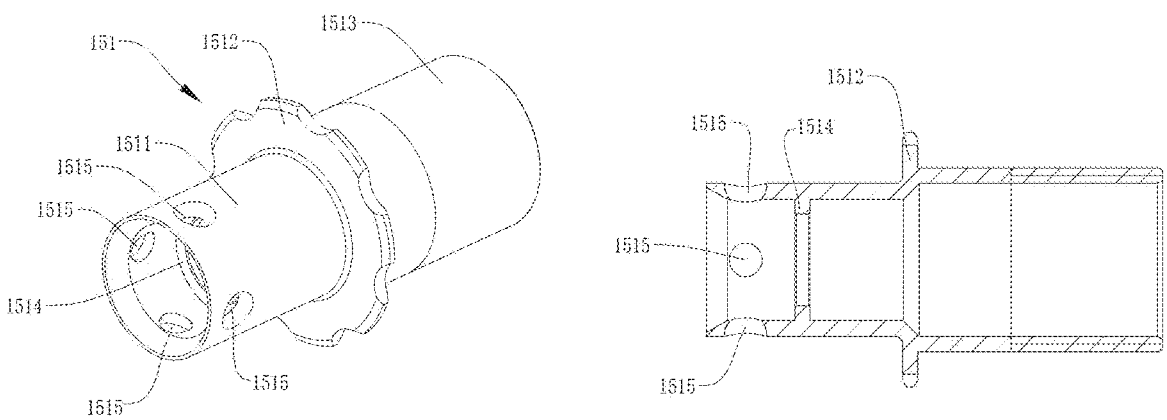
Figure 9
Figure 9A
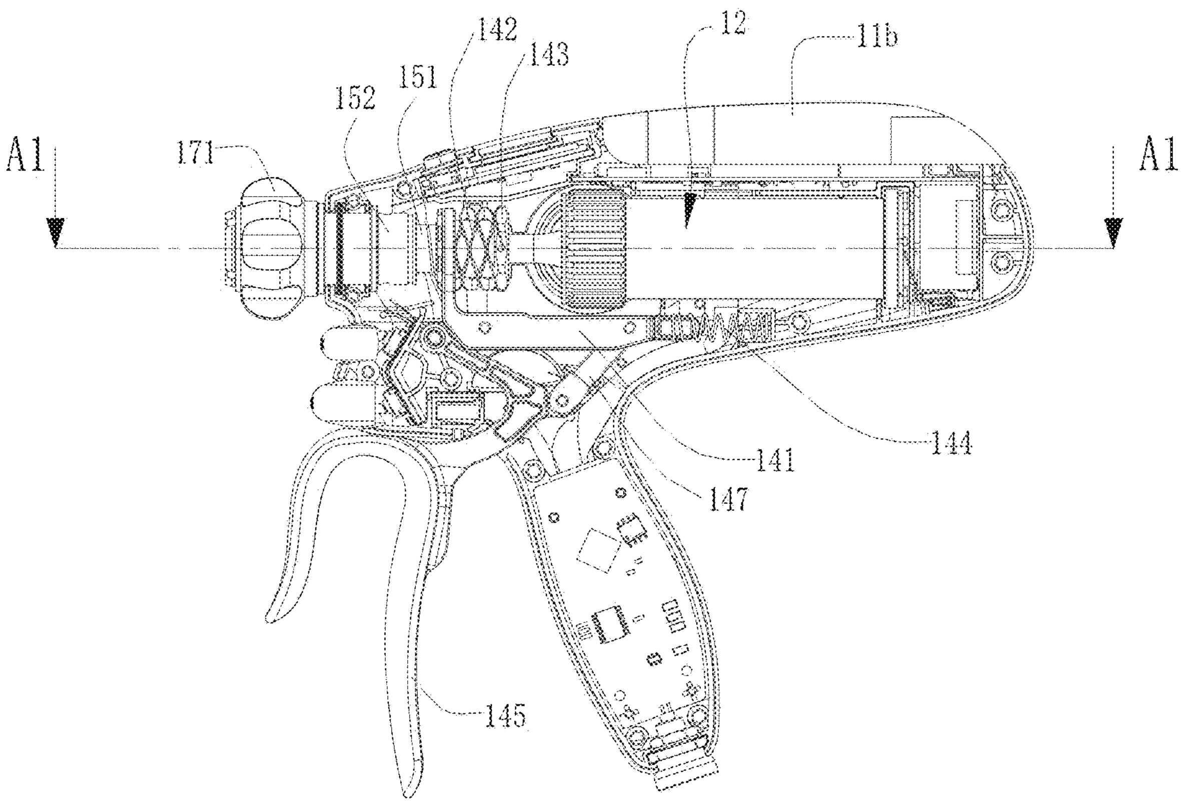
Figure 10

ULTRASONIC SCALPEL HANDLE, ULTRASONIC SCALPEL AND ULTRASONIC SCALPEL SYSTEM

CROSS-REFERENCE TO RELATED APPLICATIONS

This application is the U.S. National Phase under 35. U.S.C. § 371 of International Application PCT/CN2021/125632, filed Oct. 22, 2021, which claims priority to Chinese Patent Application No. 202011212999.8, filed Nov. 4, 2020, Chinese Patent Application No. 202120458579.1, filed Mar. 3, 2021, and Chinese Patent Application No. 202110721818.2, filed Jun. 28, 2021. The disclosures of the above-described applications are hereby incorporated by reference in their entirety.

TECHNICAL FIELD

The present disclosure relates to the technical field of medical apparatus and instruments, and in particular, to an ultrasonic scalpel handle, an ultrasonic scalpel and an ultrasonic scalpel system.

BACKGROUND

As a surgical equipment using ultrasonic energy, ultrasonic scalpel is used in various endoscopic surgery and conventional surgery, mainly for hemostatic separation of soft tissue and tissue coagulation. With the popularization of minimally invasive surgery, ultrasonic scalpel has become a conventional surgical instrument and is widely used.

At present, the ultrasonic scalpel system on the market is mainly composed of a host with an ultrasonic generator, a handle, a cutting tool, and a transducer. Before the operation, the handle, the cutting tool, and the transducer need to be assembled and installed on the host to be used, wherein the cutting tool also needs to be installed with an external torque wrench. This type of ultrasonic scalpel system has a large number of components and occupies a large space. At the same time, there are many problems such as cumbersome installation, shaking of the cutting tool relative to the handle after installation, and large matching dispersion of the host, transducer, cutting tool and other components, resulting in poor performance consistency and high failure rate of the ultrasonic scalpel.

SUMMARY

The first purpose of the present disclosure is to provide a novel ultrasonic scalpel handle, to solve one or more problems in the prior art.

To achieve the above purpose, a technical solution employed by the present disclosure is: An ultrasonic scalpel handle comprises a handle housing and a transducer assembly, the handle housing has an accommodating cavity, the transducer assembly is disposed in the accommodating cavity, and the ultrasonic scalpel handle further comprises a connecting assembly disposed in the accommodating cavity and for connecting to a cutting tool, the connecting assembly comprises:

- a connector, the axis line of the connector extending in a front-rear direction, the connector having a hollow channel penetrating in a front-rear direction, the circumferential side wall of the connector being provided with a plurality of through holes, and all the through holes being distributed at intervals in the circumferential direction and communicated with the hollow channel;
- rolling balls, the number of the rolling balls being the same as or less than the number of the through holes, and the rolling balls being radially movably arranged in the through holes;
- a ball cap, the ball cap being sleeved on the front portion of the connector in a manner that can relatively slide in the front-rear direction, and an inner peripheral wall of the ball cap being provided with a yielding structure and a position-limit structure, when the position-limit structure is located at the outer circumferences of the through holes, the rolling balls are at least partially located in the hollow channel; when the yielding structure is located at the outer circumferences of the through holes, the rolling balls are located outside the hollow channel;
- a first elastic element, the first elastic element being disposed between the connector and the ball cap, and driving the ball cap to move forward or backward with respect to the connector so as to position the position-limit structure at the outer circumferences of the through holes.

In some embodiments, the yielding structure is located at the front side of the position-limit structure, and the first elastic element provides the force required for the ball cap to move forward with respect to the connector.

In some embodiments, the diameter of the through holes is tapered from outside to inside in the radial direction of the connector, and the bottom diameter of the through holes is smaller than the diameter of the rolling balls.

In some embodiments, the ball cap has a sliding cylinder portion, a pushing portion and a position-limit cylinder portion successively connected from front to back, the inner diameter of the sliding cylinder portion is larger than that of the position-limit cylinder portion, and the pushing portion is a conical cylinder with a tapered inner diameter from front to back, wherein the inner circumferential wall of the sliding cylinder portion forms the yielding structure, and the inner circumferential wall of the position-limit cylinder portion forms the position-limit structure.

Further, the connector is provided with a position-limit ring, the position-limit ring is located in the hollow channel, and the position-limit ring is located behind the through holes.

In some embodiments, the ultrasonic scalpel handle further comprises a driving mechanism for driving the connecting assembly to move forward and backward, and the driving assembly comprises at least:

- a slider, the slider being slidingly arranged on the handle housing, and the slider being connected to the connector;
- a second elastic element, the second elastic element providing the force required for the slider to move forward;
- a handgrip, the handgrip being rotatably arranged on the handle housing, and at least part of the handgrip being located outside the handle housing;
- a linkage assembly, the linkage assembly being arranged between the handgrip and the slider and being used to drive the slider to slide backward and forward when rotating the handgrip.

Further, the slider is provided with a sleeve section slidably sleeved on the connector, the rear portion of the connector is adjustably provided with an adjusting nut, and a third elastic element is provided between the adjusting nut and the sleeve section to drive the two away from each other in the front-rear direction.

In some embodiments, the transducer assembly can be accommodated in the accommodating cavity in a manner that can rotate about its own axis, the transducer assembly comprises a transducer shell and a transducer, the transducer shell has a hollow cavity penetrating in a front-rear direction, at least a rear portion of the transducer is accommodated in the hollow cavity.

Further, the transducer assembly further comprises an electric plate provided at a rear portion of the transducer shell, the electric plate is provided with a conductive portion, the transducer is electrically connected to the conductive portion, an elastic conductive element is further provided in the accommodating cavity of the handle housing, the elastic conductive element abuts forward against the rear end face of the electric plate, and in the process that the transducer assembly rotates about its own axis with respect to the handle housing, the elastic conductive element is always in contact with the conductive portion to maintain electric connection.

In some embodiments, the conductive portion comprises a first conductive portion and a second conductive portion insulated from each other, the transducer has a first electric lead and a second electric lead, the first electric lead is electrically connected to the first conductive portion, and the second electric lead is electrically connected to the second conductive portion; the elastic conductive element has a first elastic conductive element and a second elastic conductive element disposed independently, the first elastic conductive element abuts against the first conductive portion, and the second elastic conductive element abuts against the second conductive portion.

In some embodiments, the first conductive portion and the second conductive portion are in the shape of a disc or ring taking the axis line of the transducer assembly as a rotation center.

In some embodiments, the electric plate comprises a plate body, a first conductive piece and a second conductive piece which are fixed on the plate body and made of metal materials, the first conductive piece forms the first conductive portion, the second conductive piece forms the second conductive portion, the first elastic conductive element abuts against the rear side of the first conductive piece, and the second elastic conductive element abuts against the rear side of the second conductive piece.

In some embodiments, the second conductive piece is in the shape of a ring and circumferentially disposed on the circumferential outer side of the first conductive piece, and the first conductive piece and the second conductive piece are disposed at intervals in the radial direction of the electric plate.

In some embodiments, the plate body is provided with a first perforated hole and a second perforated hole penetrating in its own thickness direction, the first electric lead runs through the first perforated hole and is fixedly connected to the first conductive piece, and the second electric lead runs through the second perforated hole and is fixedly connected to the second conductive piece.

In some embodiments, the first elastic conductive element and the second elastic conductive element are both elastic pieces made of metal materials, an end portion of the first conductive element and an end portion of the second elastic conductive element are fixedly arranged in the handle housing respectively, the other end portion of the first elastic conductive element presses forward against the first conductive portion, and the other end portion of the second elastic conductive element presses forward against the second conductive portion.

In some embodiments, the ultrasonic scalpel handle further comprises a power connecting wire, an end portion of the power connecting wire is fixedly and electrically connected to the elastic conductive element, and the other end portion of the power connecting wire goes out of the accommodating cavity from a lower portion of the handle housing.

In some embodiments, the ultrasonic scalpel handle further comprises a transducer constraint assembly for limiting the rotation of the transducer assembly, and the transducer constraint assembly is divided into two groups on the left and right sides of the transducer assembly.

In some embodiments, each group of transducer constraint assembly comprises a pressing bar extending in the front-rear direction, the pressing bar is rotatably arranged on the handle housing around a central line of rotation extending in an up-down direction, the rear portion of the pressing bar is provided with a pressing and holding portion, a constraint structure is arranged between the inner side of the pressing and holding portion and the outer circumference of the transducer shell to limit the rotation of the transducer shell, the transducer constraint structure has a constraint state and a release state, when in the constraint state, the two pressing and holding portions on the left and right sides abut against the outer circumference of the transducer shell respectively; when in the release state, the two pressing and holding portions are separated from the outer circumference of the transducer shell, and the transducer constraint assembly further comprises an elastic element for driving the pressing bar to rotate so that the pressing and holding portion moves away from the transducer shell.

In some embodiments, the transducer shell is cylindrical, and the pressing and holding portion is an arc-shaped sheet fitting the outer circumference of the transducer shell.

In some embodiments, the constraint structure comprises a first tooth portion arranged on the outer circumference of the transducer shell, a second tooth portion arranged on the inner side of the pressing and holding portion, and when the transducer constraint structure is in the constraint state, the first tooth portion engages the second tooth portion.

In some embodiments, the constraint structure is a positioning structure arranged between the outer circumference of the transducer shell and the inner surface of the pressing and holding portion and realizing the circumferential positioning of the transducer shell by interaction; or is a friction-increasing structure arranged between the outer circumference of the transducer shell and the inner surface of the pressing and holding portion for increasing the friction between the two and limit the rotation of the transducer shell.

In some embodiments, left and right portions of the transducer shell are provided with operating windows, the outer sides of the operating windows are covered with a rubber cover capable of elastic deformation, and the two pressing and holding portions block the two operating windows from the inner side of the handle housing, respectively.

The second purpose of the present disclosure is to provide an ultrasonic scalpel having the aforementioned ultrasonic scalpel handle.

To achieve the above purpose, a technical solution employed by the present disclosure is:

An ultrasonic scalpel, comprises the foregoing ultrasonic scalpel handle, and further comprises a cutting tool detachably mounted on the ultrasonic scalpel handle, wherein the cutting tool comprises an inner tube, an outer tube and a tool bar which extend in the front-rear direction, wherein the tool bar runs through the inner tube, the outer tube is sleeved outside the inner tube, the tool bar and the outer tube are fixed to each other and are arranged in a manner that can move synchronously with respect to the inner tube forward and backward, the transducer assembly at least comprises a transducer, the transducer has a horn shaft which extends in the front-rear direction, the inner tube has a inner tube body and a mounting boss extending rearward from the rear end of the inner tube body, the outer diameter of the mounting boss is larger than the outer diameter of the inner tube body, a position-limit surface is formed at the position where the inner tube body is connected to the mounting boss, the outer circumference of the mounting boss is a conical inclined surface with gradually increasing outer diameter from rear to front, the tool bar runs through the hollow channel in a manner that can slide in the axial direction, a rear end portion of the tool bar is fixedly connected with the horn shaft, the rolling balls are embedded in the through holes in a fitted manner, the rolling balls are at least partially located in the hollow channel, and the position-limit surface is located behind the rolling balls.

In some embodiments, the rear portion of the tool bar is threaded to the front portion of the horn shaft, the tool bar is disposed coaxially with the horn shaft, the ultrasonic scalpel handle further comprises a self-tightening assembly arranged on the front portion of the handle housing and used to drive the cutting tool to rotate around its own axis.

Further, the self-tightening assembly comprises an outer ring, a rotary knob inner sleeve, and an elastic piece arranged between the outer circumference of the knob inner sleeve and the inner circumference of the outer ring, wherein the inner circumference of the out ring is provided with a plurality of positioning grooves, each of the positioning grooves extends in the front-rear direction, the outer periphery of the rear portion of the outer tube is provided with a plurality of ribs at intervals extending in the front-rear direction, and the ribs fit the positioning grooves one-to-one correspondingly.

To achieve the above purpose, another technical solution employed by the present disclosure is: An ultrasonic scalpel, comprises an ultrasonic scalpel handle, and a cutting tool detachably connected to the ultrasonic scalpel handle, the cutting tool comprises an inner tube, an outer tube and a tool bar which extend in the front-rear direction, wherein the tool bar runs through the inner tube, the outer tube is sleeved outside the inner tube, the ultrasonic scalpel handle comprises a handle housing and a transducer assembly, and the transducer assembly at least comprises a transducer, the transducer has a horn shaft which extends in the front-rear direction, the ultrasonic scalpel handle further comprises a connecting assembly, the connecting assembly comprises:

a connector, the axis line of the connector extending in a front-rear direction, the connector having a hollow channel through which the inner tube can slide in from front to rear, the circumferential side wall of the connector being provided with a plurality of through holes, and all the through holes being distributed at intervals in the circumferential direction and communicated with the hollow channel;

rolling balls, the number of the rolling balls being the same as the number of the through holes;

a ball cap, the ball cap being sleeved on the front portion of the connector in a manner that can slide in the front-rear direction, a yielding channel that can accommodate the rolling balls being formed between the inner circumferential wall of the ball cap and the outer circumferential wall of the connector, and a position-limit structure being further provided on the ball cap for limiting the rolling balls in the through holes;

a first elastic element, the first elastic element being disposed between the connector and the ball cap, and driving the ball cap to move forward, such that the position-limit structure limits the rolling balls in the through holes;

the inner tube has a inner tube body and a mounting boss extending rearward from the rear end of the inner tube body, the outer diameter of the mounting boss is larger than the outer diameter of the inner tube body, a position-limit surface is formed at the position where the inner tube body is connected to the mounting boss, and the outer circumference of the mounting boss is a conical inclined surface with gradually increasing outer diameter from rear to front;

the tool bar runs through the hollow channel in a manner that can slide in the axial direction, a rear end portion of the tool bar is fixedly connected to the horn shaft, the rolling balls are embedded in the through holes in a fitted manner, the rolling balls are at least partially located in the hollow channel, and the position-limit surface is located behind the rolling balls.

In some embodiments, the connector is provided with a position-limit ring, which is located in the hollow channel, the tool bar relatively sliably runs through the position-limit ring, and the mounting boss of the inner tube is limited between the position-limit ring and the plurality of rolling balls in the front-rear direction.

In some embodiments, the ball cap has a sliding cylinder portion, a pushing portion and a position-limit cylinder portion successively connected from front to back, the inner diameter of the sliding cylinder portion is larger than that of the position-limit cylinder portion, and the pushing portion is a conical cylinder with a tapered inner diameter from front to back, wherein the yielding channel is formed between the sliding cylinder portion and the connector, and the inner circumferential wall of the position-limit cylinder portion forms the position-limit structure.

In some embodiments, the diameter of the through holes is tapered from outside to inside in the radial direction of the connector, and the bottom diameter of the through holes is smaller than the diameter of the rolling balls.

In some embodiments, the inner tube is arranged coaxially with the outer tube, the inner tube runs through the tube cavity of the outer tube in a manner that can slide in the axial direction, a cutting tool position-limit structure is provided between the inner tube and the outer tube to limit the relative sliding displacement of the two along the axial direction, and the tool bar is fixed to the outer tube so as to maintain synchronous movement.

Further, the ultrasonic scalpel handle further comprises a driving mechanism for driving the connecting assembly to move forward and backward so as to cause the inner tube to move forward and backward with respect to the outer tube, and the driving assembly comprises at least:

a slider, the slider being slidingly arranged on the handle housing, and the slider being connected to the connector;

a second elastic element, the second elastic element providing the force required for the slider to move forward;

- a handgrip, the handgrip being rotatably arranged on the handle housing, and at least part of the handgrip being located outside the handle housing;
- a linkage assembly, the linkage assembly being arranged between the handgrip and the slider and being used to drive the slider to slide forward and backward when rotating the handgrip.

More further, the slider is provided with a sleeve section slidably sleeved on the connector, the rear portion of the connector is adjustably provided with an adjusting nut, and a third elastic element is provided between the adjusting nut and the sleeve section to drive the two away from each other in the front-rear direction.

In some embodiments, the rear portion of the cutting tool runs through the hollow channel in a manner that can rotate around its own axis line, the rear portion of the tool bar is threaded to the front portion of the horn shaft, the tool bar is disposed coaxially with the horn shaft, and the ultrasonic scalpel handle further comprises a self-tightening assembly arranged on the front portion of the handle housing and used to drive the cutting tool to rotate around its own axis line.

In some embodiments, the transducer assembly further comprises a transducer shell, the transducer is fixedly mounted in the transducer shell, the transducer is disposed coaxially with the transducer shell, and the transducer assembly is disposed in the handle housing in a manner that can rotate around its own axis line;

- the transducer assembly further comprises an electric plate provided at a rear portion of the transducer shell, the electric plate is provided with a conductive portion, the transducer is electrically connected to the conductive portion, an elastic conductive element is further provided in the handle housing, the elastic conductive element abuts forward against the rear end face of the electric plate, and in the process that the transducer assembly rotates about its own axis with respect to the handle housing, the elastic conductive element is always in contact with the conductive portion to maintain electric connection.

The third purpose of the present disclosure is to provide an ultrasonic scalpel system having the aforementioned ultrasonic scalpel.

To achieve the above purpose, a technical solution employed by the present disclosure is: An ultrasonic scalpel system, comprises the foregoing ultrasonic scalpel, and a power adapter for supplying energy to the ultrasonic scalpel, wherein, a connecting wire of the power adapter extends downward from the lower portion of the ultrasonic scalpel handle.

Due to the use of the above technical solutions, the present disclosure has the following advantages over the prior art: In the ultrasonic scalpel handle and the ultrasonic scalpel of the present disclosure, the cutting tool is easy to mount and operate, and at the same time, it can realize stable and reliable connection between the cutting tool and the ultrasonic scalpel handle, so that the cutting tool does not shake during a surgery operation, the operation is more accurate, and the overall texture of the ultrasonic scalpel is enhanced. At the same time, the ultrasonic scalpel system comprises only three components, and is easier to store and use.

BRIEF DESCRIPTION OF THE DRAWINGS

FIG. 4 is a schematic three-dimensional diagram of a cutting tool of the present disclosure;

FIG. 5 is a front view of an inner tube of a cutting tool of the present disclosure;

FIG. 6 is a schematic structure diagram of a cutting tool, a connecting assembly and a driving mechanism of the present disclosure;

FIG. 9 is a schematic overall structure diagram of a connector in the connecting assembly of the present disclosure; FIG. 9A is a schematic longitudinal sectional diagram of FIG. 9;

FIG. 10 is a schematic inner structure diagram of an ultrasonic scalpel handle, wherein the cutting tool has not been mounted into the handle;

Wherein, 1, ultrasonic scalpel handle; 11, handle housing; 11*a*, housing-left; 11*a*1, rubber cover-left; 11*b*, housing-right; 11*b*1, rubber cover-right; 11*c*, top cover;

- 12, transducer assembly; 121, transducer shell; 121*a*, knurling tooth portion; 122, transducer; 1221, horn core; 1222, horn shaft; 1223, retaining ring; 123, electric plate; 1230, plate body; 123*a*, first conductive piece; 123*b*, second conductive piece; 123*c*, first perforated hole; 123*d*, second perforated hole; 124, connecting screw; 125, rubber gasket; 126, rubber ring; 127, front retaining cover; 128, rear sealing ring; 129, screw;

13, elastic conductive element; 131, first elastic conductive element; 132, second elastic conductive element;

14, driving mechanism; 141, slider; 141*a*, sleeve section; 141*b*, sliding portion; 142, third elastic element (wave spring); 143, adjusting nut; 144, second elastic element (spring); 145, handgrip; 146, pin shaft; 147, hinge;

15, connecting assembly; 151, connector; 1511, front sleeve; 1512, position-limit retaining ring; 1513, rear sleeve; 1514, position-limit ring; 1515, through hole; 152, ball cap; 152*a*, sliding cylinder portion; 152*b*, pushing portion; 152 *c*, position-limit cylinder portion; 153, rolling ball; 154, first elastic element (spring);

16, transducer constraint assembly; 161, pressing bar; 161*a*, pressing and holding portion; 162, shaft; 163, torsion spring;

17, self-tightening assembly; 171, outer ring; 172, rotary knob inner sleeve; 173, elastic piece;

181, display screen; 182, perspective window; 183, function key; 184, front key; 191, circuit board; 192, front key FPC group; 193, loudspeaker; 194, PCB group; 195, transformer; 196, connection socket; 197, protective cover; 198, power line;

2. cutting tool; 21, outer tube; 22, inner tube; 221, inner tube body; 222, mounting boss; 22*a*, position-limit surface; 22*b*, conical inclined surface; 22*c*, waist slot; 23, clamp; 24, outer tube joint; 241, spline tooth; 25, tool bar; 251, tool bar head;

3. power adapter; 31, connecting wire; 4, pedal switch.

DETAILED DESCRIPTION OF EXEMPLARY EMBODIMENTS

In the following, the technical solutions of the present disclosure are further set forth by combining the drawings and specific embodiments.

To facilitate the description of the relative positions of the components in the ultrasonic scalpel, the above and following descriptions of the front-rear direction are defined with reference to the direction observed by the operator while holding the ultrasonic scalpel for operation, where the position of the ultrasonic scalpel acting on the surgical site is front, and the position of the ultrasonic scalpel near the body is rear.

Figure 1:
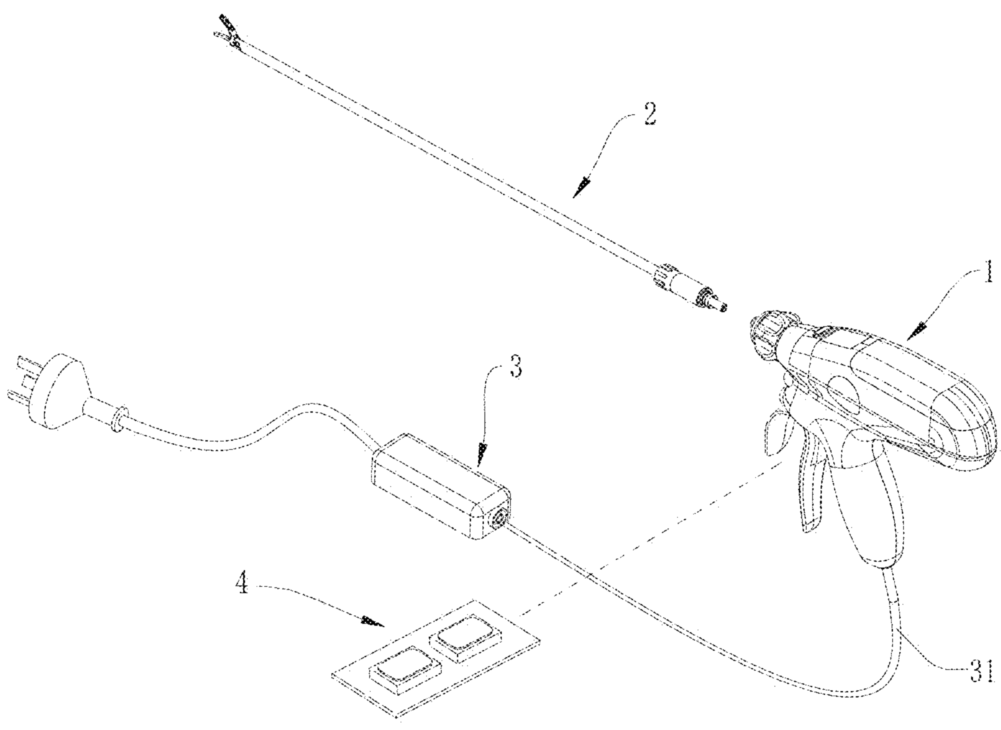
FIG. 1 is a schematic structure diagram of an ultrasonic scalpel system of the present disclosure.
Figure 2:
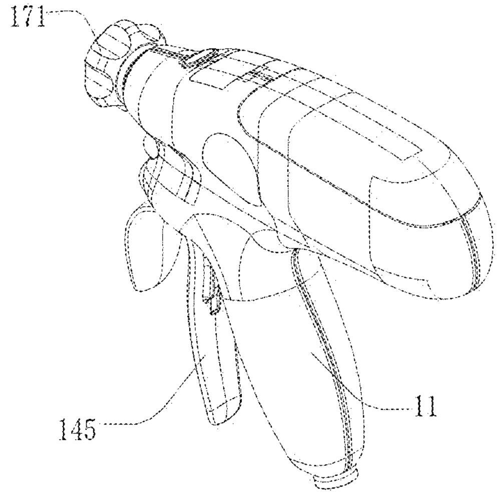
FIG. 2 is a schematic structure diagram of an ultrasonic scalpel handle of the present disclosure.

Referring to the ultrasonic scalpel system shown in FIG. 1, it comprises an ultrasonic scalpel, and a power adapter 3 for supplying energy to the ultrasonic scalpel, a pedal switch 4 optionally provided for operating control such as turning the ultrasonic scalpel on and off, wherein the ultrasonic scalpel comprises an ultrasonic scalpel handle 1, and a cutting tool 2 detachably mounted on the ultrasonic scalpel handle 1.

Referring to FIG. 4 and FIG. 5, the cutting tool 2 comprises an inner tube 22, an outer tube 21 and a tool bar 25 all of which extend in the front-rear direction, here, the inner tube 22 runs through the tube cavity of the outer tube 21 in a manner that can slide in the front-rear direction, and the two are disposed coaxially, and a cutting tool position-limit structure is provided between the inner tube 22 and the outer tube 21 to limit the relative sliding displacement of the two in the axial direction, the cutting tool position-limit structure here comprises a waist slot 22*c* opened on the inner tube 22, and a position-limit pin (not shown) fixedly arranged on the outer tube 21, the position-limit pin is inserted into the waist slot 22*c* in a sliding fit manner to avoid the forward or backward offside slip of the inner tube 22 relative to the outer tube 21. The tool bar 25 runs through the tube cavity of the inner tube 22 in a manner that can slide in its own length direction, the rear portion thereof extends backwards behind the inner tube 22, and the front portion thereof has a tool bar head 251. The tool bar 25 is connected to the outer tube 21 through a position-limit pin to maintain relatively fixed, so that the tool bar 25 and the outer tube 21 can maintain synchronous motion, and the synchronous motion mainly comprises synchronous rotation and synchronous forward and backward movement relative to the inner tube 22.

The cutting tool 2 further comprises a clamp 23 located in the front, which is rotatably arranged between the front portion of the inner tube 22 and the front portion of the outer tube 21, the relative sliding of the inner tube 22 relative to the outer tube 21 in the front-rear direction drives the clamp 23 to open or close relative to the tool bar head 251, so as to achieve the operation of clamping or hemostasis of the soft tissue of the surgical object.

The rear portion of the outer tube 21 is further fixedly provided with an outer tube joint 24, the outer tube joint 24 has a plurality of spline teeth 241 distributed at intervals in the circumferential direction, and ribs of the spline teeth 241 extend in the front-rear direction. The inner tube 22 has an inner tube body 221 and a mounting boss 222 extending rearward from the inner tube body 221, the mounting boss 222 and the inner tube body 221 are essentially integrated, the outer diameter of the mounting boss 222 is larger than the outer diameter of the inner tube body 221, a position-limit surface 22*a* is formed at the position where they are connected, the position-limit surface 22*a* is a conical surface with gradually increasing outer diameter from front to rear, and outer circumference of the mounting boss 222 is a conical inclined surface 22*b* with gradually increasing outer diameter from rear to front.

Referring to the drawings, the ultrasonic scalpel handle 1 comprises a handle housing 11 and a transducer assembly 12, the handle housing 11 comprises a housing-left 11*a* and a housing-right 11*b* that are fixedly connected and fitted, and a top cover 11*c* at the top, and the handle housing 11 has an accommodating cavity, the transducer assembly 12 can be accommodated in the accommodating cavity in a manner that can rotate about its own axis.

Figure 16:
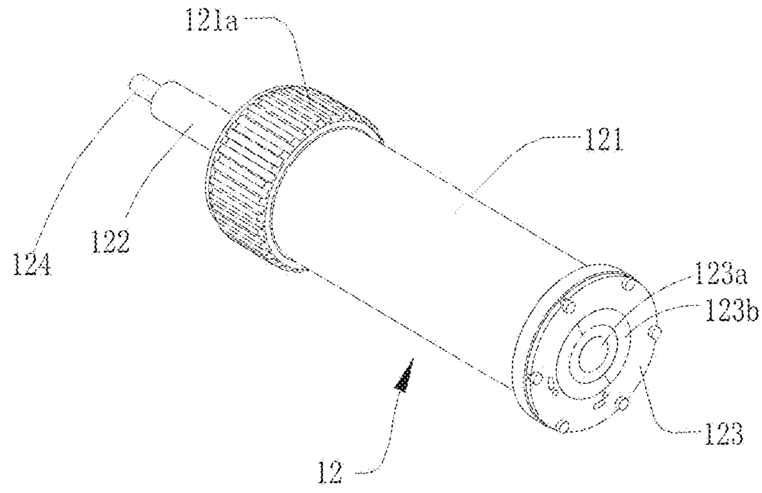
FIG. 16 is a schematic overall structure diagram of a transducer assembly of the present disclosure.
Figure 17:
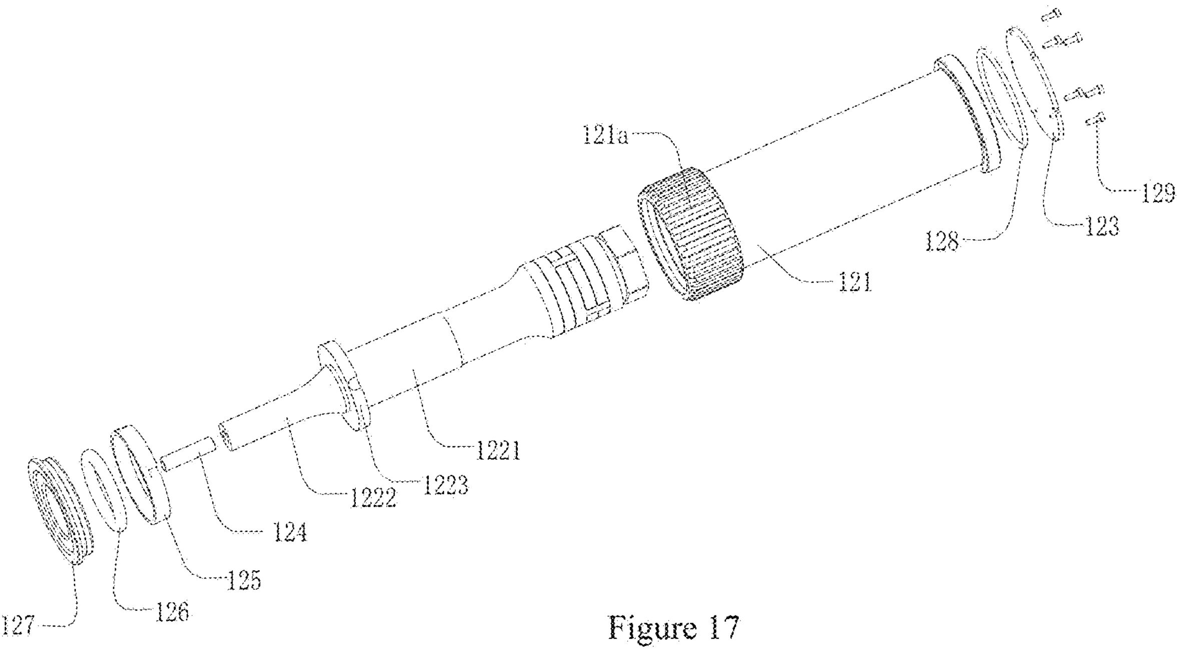
FIG. 17 is a schematic exploded structure diagram of the transducer assembly of FIG. 16.
Figure 18:
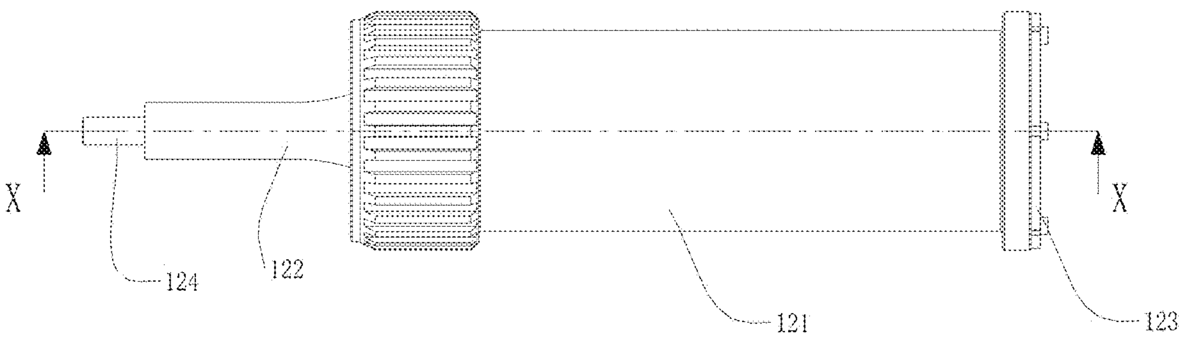
FIG. 18 is a front view of the transducer assembly of FIG. 16.
Figure 19:
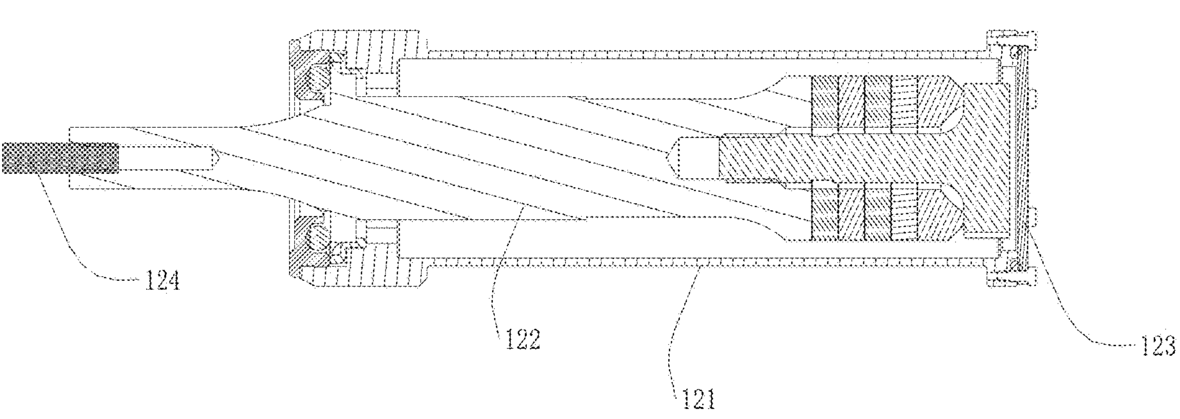
FIG. 19 is a schematic sectional view along Line X-X in FIG. 18.
Figure 20:
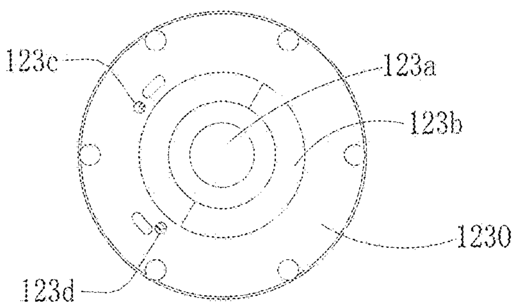
FIG. 20 is a right view of the transducer assembly of FIG. 16.

Referring to FIG. 16 to FIG. 18, the transducer assembly 12 comprises a transducer shell 121 and a transducer 122, the transducer shell 121 has a hollow cavity penetrating in a front-rear direction, the transducer 122 comprises a horn shaft 1222 and a horn core 1221 successively arranged in the axial direction, the horn core 1221 is totally contained in the hollow cavity of the transducer shell 121, and the front portion of the horn shaft 1222 extends outside the hollow cavity and is used to connect with the cutting tool 2.

The transducer assembly 12 further comprises an electric plate 123 provided on the rear portion of the transducer shell 121, the electric plate 123 is provided with a conductive portion, the transducer 122 is electrically connected to the conductive portion via a wire. An elastic conductive element 13 is further provided in the accommodating cavity of the handle housing 11, the elastic conductive element 13 abuts forward against the rear end face of the electric plate 123, and in the process that the transducer assembly 12 rotates about its own axis with respect to the handle housing 11, the elastic conductive element 13 is always in contact with the conductive portion to maintain electric connection.

Specifically, the conductive portion comprises a first conductive portion and a second conductive portion insulated from each other, the transducer 122 has two electric leads—a first electric lead and a second electric lead (not shown), the first electric lead is electrically connected to the first conductive portion, and the second electric lead is electrically connected to the second conductive portion. The elastic conductive element 13 has a first elastic conductive element 131 and a second elastic conductive element 132 disposed independently and insulated from each other, the first elastic conductive element 131 abuts against the first conductive portion, and the second elastic conductive element 132 abuts against the second conductive portion. The above first conductive portion and the second conductive portion are in the shape of a disc or ring taking the axis line of the transducer assembly 12 as a rotation center, in this way, in the process that the transducer assembly 12 rotates about its own axis, the first elastic conductive element 131 and the second elastic conductive element 132 can keep to abut against the first conductive portion and the second conductive portion respectively.

In this embodiment, the electric plate 123 comprises a plate body 1230, and a first conductive piece 123*a* and a second conductive piece 123*b* which are fixed on the plate body 1230 and made of metal materials, wherein, the first conductive piece 123*a* is in the shape of a disc, and the second conductive piece 123*b* is in the shape of a ring and circumferentially disposed on the circumferential outer side of the first conductive piece 123*a*, and the first conductive piece 123*a* and the second conductive piece 123*b* are disposed at intervals in the radial direction of the electric plate 123, that is, the outer circumferential wall of the first conductive piece 123*a* and the inner circumferential wall of the second conductive piece 123*b* have a distance in the radial direction of the electric plate 123. The first conductive piece 123*a* forms the first conductive portion, and the second conductive piece 123*b* forms the second conductive portion.

A first perforated hole 123*c* and a second perforated hole 123*d* are opened on the plate body 1230 penetrating in its own thickness direction, the first electric lead runs through the first perforated hole 123*c* and fixedly to the first conductive piece 123*a* by means of welding to realize electric connection, and the second electric lead runs through the second perforated hole 123*d* and fixedly to the second conductive piece 123*b* by means of welding to realize electric connection.

Figure 3:
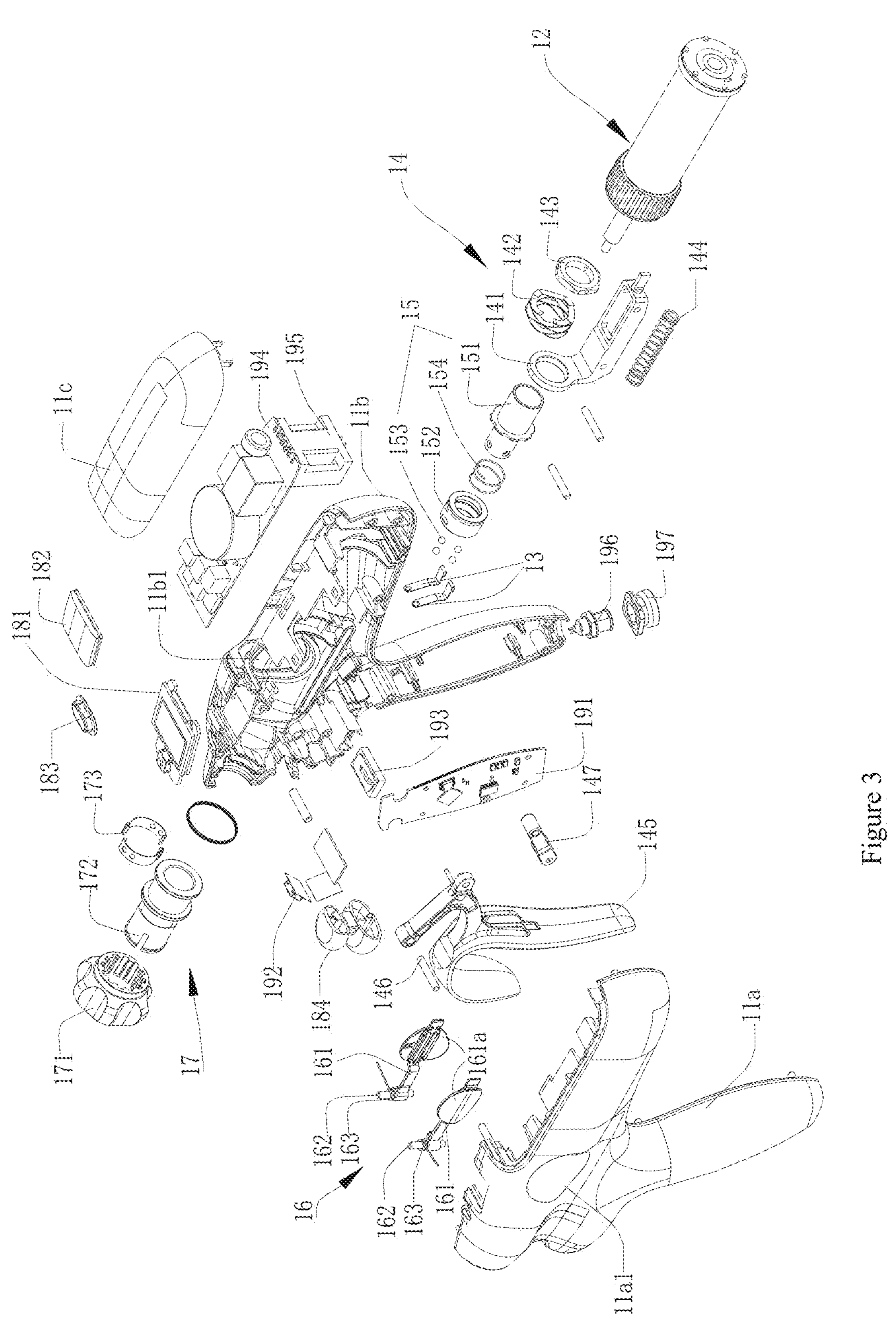
FIG. 3 is a schematic exploded structure diagram of an ultrasonic scalpel handle of the present disclosure.
Figure 21:
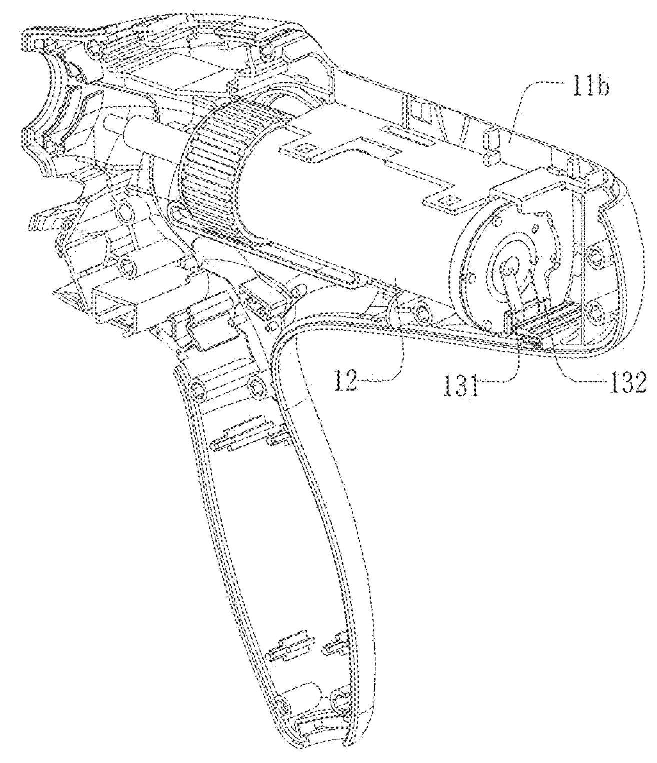
FIG. 21 is a schematic diagram of the connection structure between the transducer assembly and the elastic conductive element.

Referring to FIG. 3 and FIG. 21, the first elastic conductive element 131 and the second elastic conductive element 132 are both elastic pieces made of metal materials, the lower end portion of the first elastic conductive element 131 and the lower end portion of the second elastic conductive element 132 are fixedly disposed in the handle housing 11 respectively, the upper end portion of the first elastic conductive element 131 presses forward against the rear side of the first conductive portion 123*a*, and the upper end portion of the second elastic conductive element 132 presses forward against the rear side of the second conductive portion 123*b*.

In this way, it only needs to connect the two conductive wires of the power cord to the first elastic conductive element 131 and the second elastic conductive element 132 respectively, then the power cord can be introduced from the lower portion of the handle housing 11 to connect to the power supply, in this way, in the process that the transducer assembly 12 rotates about its own axis in the handle housing 11, the power cord does not rotate with it, such that a series of problems of the large arm force and easy fatigue, and knotting of the power cord, etc. caused by the power cord extending from the rear portion of the handle housing 11 are avoided.

The front portion of the horn shaft 1222 of the transducer 122 is further fixedly provided with a connecting screw 124 for detachably connecting with the cutting tool 2.

When arranging the transducer assembly 12, as shown in FIG. 16 and FIG. 17, the electric plate 123 is disk-shaped, which is fixed at the rear portion of the transducer shell 121 through multiple screws 129, and a rear sealing ring 128 is provided between the electric plate 123 and the rear end face of the transducer shell 121, so that the rear portion of the transducer shell 121 is sealed.

A retaining ring 1223 is provided on the transducer 122 at the position of the horn shaft 1222 and the horn core 1221, and its outer diameter is larger than the outer diameter of either the horn shaft 1222 or the horn core 1221, the front portion of the transducer shell 121 is further provided with a rubber gasket 125, a rubber ring 126 and a front retaining cover 127, the front retaining cover 127 is fixedly fitted to the front portion of the transducer shell 121, and the rubber ring 126 and the rubber gasket 125 are pressed between the retaining ring 1223 and the front retaining cover 127, so that the front portion of the transducer shell 121 is also sealed. Thus, the horn core 1221 is fixedly sealed in the transducer shell 121. The transducer assembly 12 is conveniently mounted into the inner cavity of the handle housing 11 as a whole component.

Figures 7, 7A, 8:
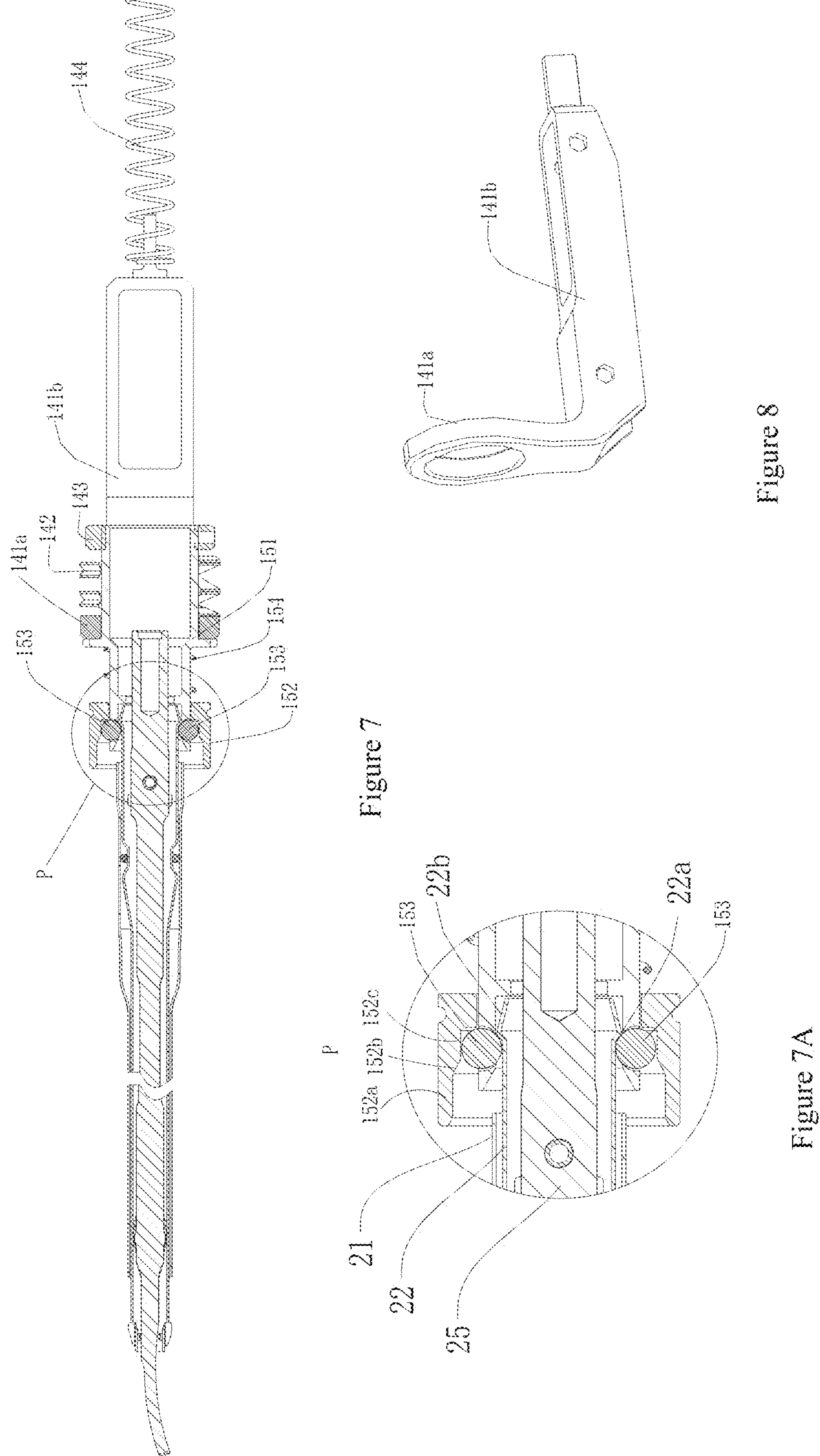
FIG. 7 is a schematic diagram of the inner structure of a cutting tool, a connecting assembly and a driving mechanism of the present disclosure.
FIG. 7A is an enlarged diagram at Part P in FIG. 7.
FIG. 8 is a schematic three-dimensional diagram of a slider of the driving mechanism of FIG. 6.

The ultrasonic scalpel handle 1 further comprises a connecting assembly 15, which is mainly used to realize a detachable connection with the inner tube 22 in the cutting tool 2, and the ultrasonic scalpel handle 1 also includes a driving mechanism 14 for driving the connecting assembly 15 to move forward and backward so as to cause the inner tube 22 to move forward and backward with respect to the outer tube 21. See FIGS. 3 to 15 for details. Wherein:

The connecting assembly 15 comprises:

a connector 151, the axis line of the connector 151 extending in a front-rear direction, here, the axis line thereof extends colinearly with the axis line of the transducer 122. The connector 151 has a hollow channel through which the inner tube 22 of the cutting tool 2 can slide in from front to rear, the circumferential side wall of the connector 151 is provided with a plurality of through holes 1515, and all the through holes 1515 are distributed at intervals in the circumferential direction and communicated with the hollow channel of the connector 151;

rolling balls 153, the number of the rolling balls 153 being the same as or less than the number of the through holes 1515, the number of the rolling balls 153 being at least two, in this embodiment, the rolling balls 153 and the through holes 1515 are both provided with four;

a ball cap 152, the ball cap 152 being sleeved on the front portion of the connector 151 in a manner that can slide in the front-rear direction, a yielding channel being formed between the inner circumferential wall of the ball cap 152 and the outer circumferential wall of the connector 151 and used for yielding during the outward movement of the rolling balls 153 relative to the through holes 1515, and a position-limit structure being formed on the ball cap 152 for limiting the rolling balls 153 in the through holes 1515 to prevent them from rolling or sliding in the yielding channel;

a first elastic element 154, here specifically a spring, the first elastic element 154 being disposed between the connector 151 and the ball cap 152, and driving the ball cap 152 to move forward so as to make the position-limit structure limit the rolling balls 153 in the through holes 1515, wherein, as shown in FIG. 6, FIG. 7 and FIG. 7A, the cutting tool 2 runs through the hollow channel of the connector 151 in a manner that can slide in the axial direction from front to rear, the rear portion of the tool bar 25 is fixedly connected to the horn shaft 1222 of the transducer 122 in a threaded connection manner, the rolling balls 153 are correspondingly embedded in the through holes 1515 in a fitted manner, the rolling balls 153 are at least partially located in the hollow channel of the connector 151, and the position-limit surface 22*a* on the inner tube 22 is located behind the rolling balls 153. In this way, the inner tube 22 is mounted on the connector 151, and can rotate relative to the connector 151, at the same time, when driving the connector 151 to move backward, it can drive the inner tube 22 to move backward relative to the outer tube 21.

Specifically, as shown in FIG. 9 and FIG. 9A, the connector 151 has a front sleeve 1511 and a rear sleeve 1513 that are connected in the axial direction, a position-limit retaining ring 1512 is formed at the position where the front sleeve 1511 and the rear sleeve 1513 are connected, the outer diameter of the position-limit retaining ring 1512 is larger than the outer diameter of the front sleeve 1511 and the outer diameter of the rear sleeve 1513. The through holes 1515 are arranged at the front end portion of the front sleeve 1511, and a position-limit ring 1514 is formed in the inner cavity of the front sleeve 1511, the tool bar 25 relatively sliably runs through the position-limit ring 1514, and the mounting boss 222 of the inner tube 22 is limited between the position-limit ring 1514 and the plurality of rolling balls 153 in the front-rear direction, so that after the inner tube 22 is mounted on the connector 151, it is fixed with the connector 151 in the axial direction, in this way, driving the forward and backward movement of the connector 151 can drive the inner tube 22 to move synchronously in the front-rear direction.

As shown in FIG. 7 and FIG. 7A, the ball cap 152 has a sliding cylinder portion 152*a*, a pushing portion 152*b* and a position-limit cylinder portion 152*c* successively connected from front to rear, the inner diameter of the sliding cylinder portion 152*a* is larger than that of the position-limit cylinder portion 152*c*, the pushing cylinder 152*b* is a conical cylinder with a tapered inner diameter from front to back, wherein, the above-mentioned yielding channel is formed between the inner circumferential wall of the sliding cylinder portion 152*a* and the outer circumferential wall of the front sleeve 1511 of the connector 151, and the rolling balls 153 can be partially contained in the yielding channel; the inner circumferential wall of the position-limit cylinder portion 152*c* forms the above position-limit structure, that is, when the position of the position-limit cylinder portion 152*c* corresponds to the positions of the through holes 1515, the distance between the inner circumferential wall of the position-limit cylinder portion 152*c* and the outer circumferential wall of the front sleeve 1511 is smaller than the diameter of the rolling balls 153, so that the rolling balls 153 are limited in the through holes 1515 and cannot move forward or backward.

The diameter of the through holes 1515 is tapered from the outside of the connector 151 to the inside along the radial direction, the bottom diameter of the through holes 1515 is smaller than the diameter of the rolling balls 153, which makes the rolling balls 153 not completely fall from the through holes 1515 to the hollow cavity of the connector 151, at the same time, it can make the rolling balls 153 at least partially located in the hollow cavity of the connector 151 and used to fit the inner tube 22 when placed in the through holes 1515 to form a limit for the forward movement of the inner tube 22.

Referring to FIG. 3, FIG. 6, FIG. 7, FIG. 10 and FIG. 15, the driving mechanism 14 comprises:

a slider 141, the slider 141 being slidingly arranged on the handle housing 11, and the slider 141 being connected to the connector 151. Specifically, the slider 141 comprises a sliding portion 141*b* and a sleeve section 141*a* arranged in an L shape, wherein the sleeve section 141*a* is sleeved on the rear sleeve 1513 of the connector 151, and the sliding portion 141*b* extends in the front-rear direction and is arranged in the handle housing 11 in a manner that can slide forward and backward;

a second elastic element 144, here specifically a spring, the second elastic element 144 being arranged between the handle housing 11 and the rear portion of the sliding portion 141*b* and providing the force required for the slider 141 to move forward;

a handgrip 145, the handgrip 145 being rotatably arranged on the handle housing 11 around the pin shaft 146, the operating part thereof being located outside the accommodating cavity of the handle housing 11, and at least part thereof being located inside the accommodating cavity of the handle housing 11;

a linkage assembly, the linkage assembly being arranged between the handgrip 145 and the slider 141 and being used to drive the slider 141 to move backward and forward when rotating the handgrip 145. Here, the linkage assembly is a mechanism comprising a hinge 147 to convert the rotation of the handgrip 145 to the sliding of the slider 141.

The driving mechanism 14 further comprises a position-adjustable adjusting nut 143 arranged at the rear portion of the connector 151, a third elastic element 142 is provided between the adjusting nut 143 and the sleeve section 141*a* to drive the two away from each other in the front-rear direction, here, the third elastic element 142 is a wave spring sleeved on the rear sleeve 1513, and the sleeve section 141*a* of the slider 141 is limited between the third elastic element 142 and the position-limit retaining ring 1512. By rotating the adjusting nut 143, the wave spring can be held in different states, so that different forces need to be applied to make the sleeve section 141*a* move backward relative to the connector 151.

As shown in FIG. 3 and FIG. 6, the ultrasonic scalpel handle 1 is further provided with a transducer constraint assembly 16, the transducer constraint assembly 16 comprises two groups disposed on the left and right sides of the transducer assembly 12, each group comprises a pressing bar 161 extending in the front-rear direction, the front portion of the pressing bar 161 is rotatably arranged on the handle housing 11 through a shaft 162 extending in an up-down direction, the rear portion of the pressing bar 161 is provided with a pressing and holding portion 161*a*, and the pressing and holding portion 161*a* is arc-shaped, and the side thereof facing the transducer assembly 12 is provided with knurling teeth; a torsion spring 163 is sleeved on the shaft 162 to drive the pressing and holding portion 161*a* to move away from the transducer assembly 12. The front portion of the transducer shell 121 of the transducer assembly 12 is also provided with a knurling tooth portion 121*a*, on which a circle of knurling teeth is formed correspondingly engaging the knurling teeth on the pressing and holding portion 161*a*.

When the pressing and holding portion 161*a* on the left and right sides simultaneously moves towards the transducer assembly 12 and is pressed against the knurling tooth portion 121 a, the transducer assembly 12 can be restricted in the circumferential direction through the engagement of the knurling teeth, thus avoiding the rotation of the transducer assembly 12. A rubber cover-left 11*al* is arranged on the housing-left 11*a* of the handle housing 11, and a rubber cover-right 11*b*1 is arranged on the housing-right 11*b*, the rubber cover-left 11*al* corresponds to the position of the pressing and holding portion 161*a* on the left side, and the rubber cover-right 11*b*1 corresponds to the position of the pressing and holding portion 161*a* on the right side, in this way, during the operation, the operator's two fingers pinch and press the rubber cover-left 11*al* and the rubber cover-right 11*b*1 to deform them, so that the pressing and holding portions 161*a* on both sides can be driven to move synchronously towards the transducer assembly 12 to realize the constraint on the rotation of the transducer assembly 12.

As shown in FIG. 3 and FIG. 6, the ultrasonic scalpel handle 1 is further provided with a self-tightening assembly 17, which comprises an outer ring 171, the rotary knob inner sleeve 172, and an elastic piece 173 arranged between the outer circumference of the rotary knob inner sleeve 172 and the inner circumference of the outer ring 171, the inner circumference of the out ring 171 is provided with a plurality of positioning grooves, each of the positioning grooves extends in the front-rear direction, and is mainly used to match the outer tube joint 24 at the rear portion of the outer tube 21 of the cutting tool 2, when the outer tube joint 24 is inserted into the outer ring 171, the spline teeth 241 thereon matches the above positioning grooves, so that the outer ring 171 and the outer tube 21 are positioned in the circumferential direction and can rotate synchronously, in this way, when the user rotates the outer ring 171, the outer tube 21 of the cutting tool 2 can be driven to rotate synchronously, and the tool bar 25 rotates synchronously, therefore, it is not necessary to use external components such as torque wrench to realize the fastening and mounting between the tool bar 25 and the transducer assembly 12, and the operation is more convenient.

Figure 11:
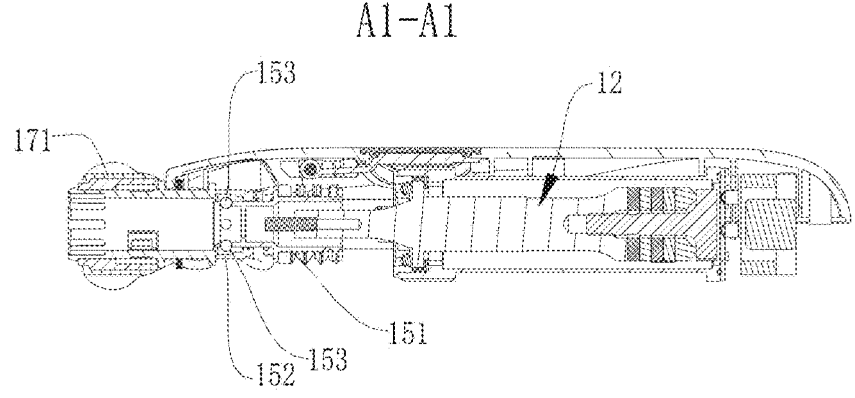
FIG. 11 is a schematic sectional view along Line A1-A1 in FIG. 10.

The following briefly describes the use method and installation method of the ultrasonic scalpel of the present disclosure:

When not in use, the ultrasonic scalpel handle 1 and the cutting tool 2 are separated from each other and stored independently, as shown in FIG. 10 and FIG. 11, at this time, in the ultrasonic scalpel handle 1, the rolling balls 153 are correspondingly located within the respective through holes 1515, and corresponds to the position of the sliding cylinder portion 152*a* of the ball cap 152.

When mounting the cutting tool 2, the rubber cover-left 11*al* and the rubber cover-right 11*b*1 are pinched to deform, so that the rotation of the transducer assembly 12 is constrained, then, the rear portion of the cutting tool 2 is inserted backward from the front portion of the ultrasonic scalpel handle 1, so that the spline teeth on the outer tube 21 of the cutting tool 2 correspond to the positioning grooves inside the outer ring 171; when continuing to insert the cutting tool 2 backward until the rear portion of the tool bar 25 touches the front portion of the transducer assembly 12, the cutting tool 2 is rotated so that the rear portion of the tool bar 25 is threaded to the horn shaft 1222 of the transducer 122.

Figure 12:
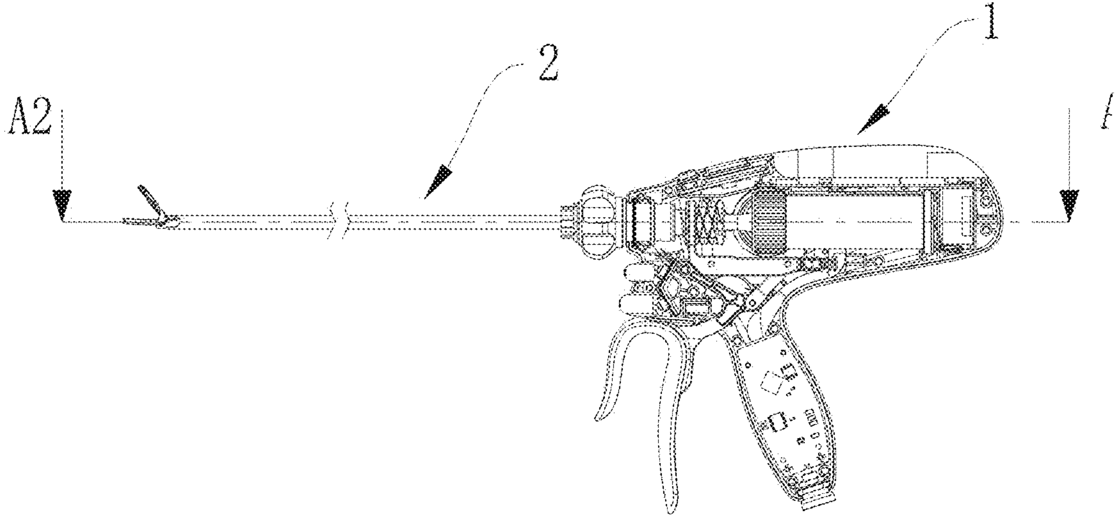
FIG. 12 is a schematic inner structure diagram of an ultrasonic scalpel handle, wherein the cutting tool has been inserted into the ultrasonic scalpel handle and the outer tube and the transducer have been connected but the inner tube has not been connected in place.
Figure 13:
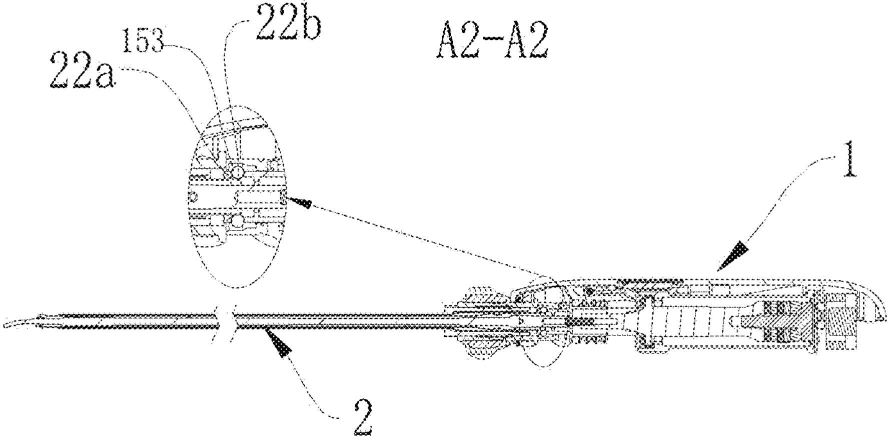
FIG. 13 is a schematic sectional view along Line A2-A2 in FIG. 12.
Figure 14:
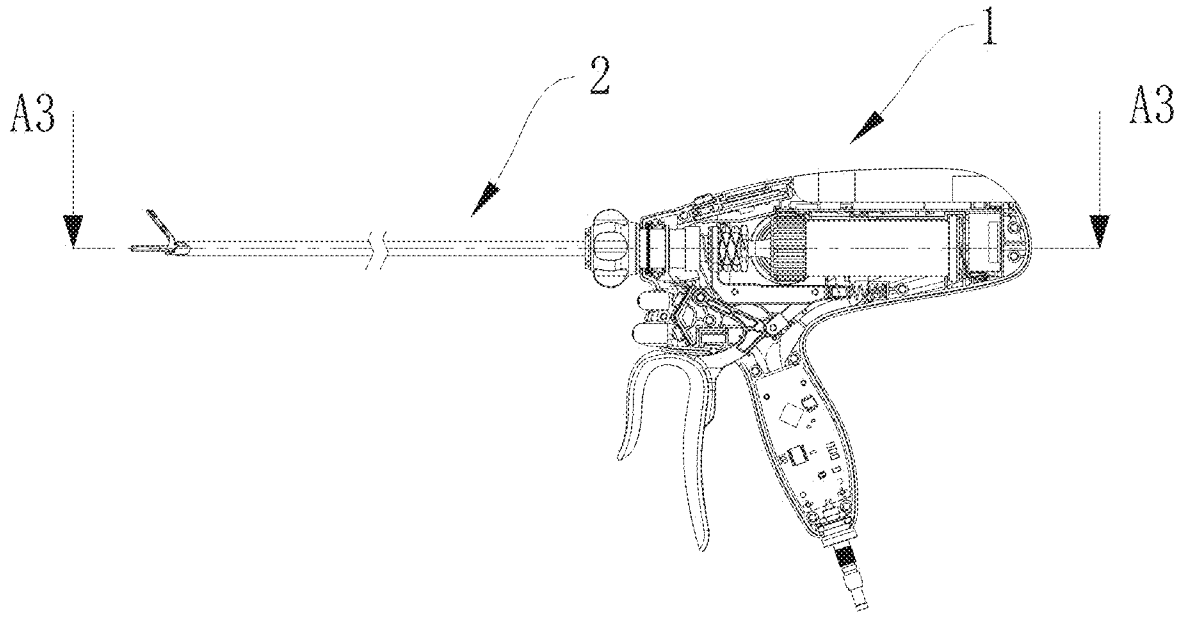
FIG. 14 is a schematic inner structure diagram of an ultrasonic scalpel, wherein the cutting tool and the ultrasonic scalpel handle have been connected.
Figure 15:
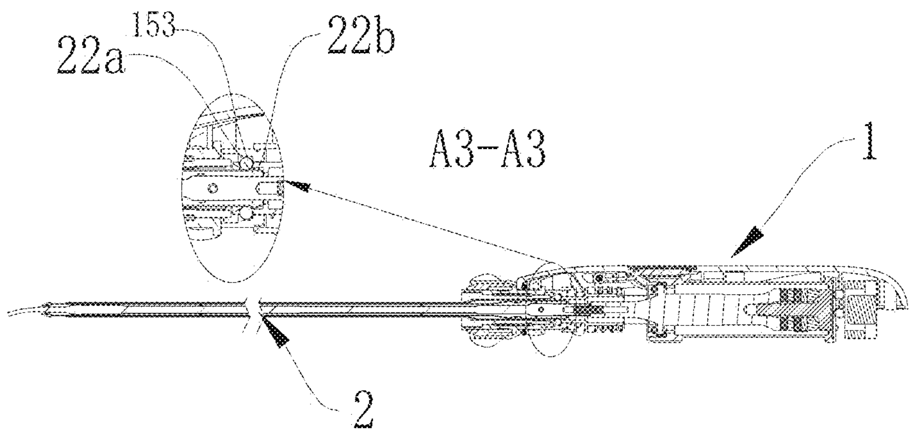
FIG. 15 is a schematic sectional view along Line A3-A3 in FIG. 14.

In the process of backward movement of the cutting tool 2, as shown in FIG. 12 and FIG. 13, the conical inclined surface 22*b* of the mounting boss 222 of the inner tube 22 first contacts the rolling balls 153, and pushes the rolling balls 153 to move upward first and enter the yielding channel, so that the inner tube 22 can move backward, and after the mounting boss 222 crosses the rolling balls 153, under the action of the first elastic element 154 and the second elastic element 144, the ball cap 152 moves forward, the pushing portion 152*b* in the ball cap 152 acts on the rolling balls 153, so that the rolling balls 153 move inward towards the through holes 1515, until the position of the position-limit cylinder portion 152*c* corresponds to the position of the through holes 1515, the rolling balls 153 are limited to the through holes 1515, and some of them extend into the hollow cavity of the connector 151, and at the same time, abut against the position-limit surface 22*b* on the front side of the mounting boss 222 to form a position limit in front of the mounting boss 222, and the mounting of the inner tube 22 is completed. Finally, the outer ring 171 is rotated to make the whole cutting tool 2 rotate accordingly, so that the thread connection between the tool bar 25 and the horn shaft 1222 of the transducer 122 is more stable, and the self-tightening assembly 17 also makes the torque of the thread connection between the horn shaft 1222 and the tool bar 25 not too large to cause damage to the transducer assembly 12.

In the process of using the ultrasonic scalpel, the user can turn the outer ring 171 to adjust the angle of the cutting tool 2; in the process of surgical operation, the operator holds the handgrip 145, and the cutting tool 2 has two different working states during the rotation of the handgrip 145, at the initial stage of the rotation of the handgrip 145, the slider 141 overcomes the force of the second elastic element 144 and moves backwards, at the same time, the slider 141 acts on the adjusting nut 143 by the wave spring of the third elastic element 142 to drive the connector 151 to move backward, the rolling balls 153 drive the inner tube 22 to move backward relative to the outer tube 21, and drive the clamp 23 to contact with the tool bar head 251, this stage realizes the clamping closure operation, which enables operations such as clamping of soft tissues; when continue to rotate the handgrip 145, the slider 141 continues to press the second elastic member 144, at this time, the second elastic member 144 is compressed and forms a spring pressure, so that the inner tube 22 is further pulled backward, and the clamp 23 is further closed to form a clamping force, and this stage can be used for operations such as soft tissue cutting, separation and hemostasis. After the operation is completed, the handgrip 145 is released, and each component will be reset under the action of the plurality of elastic elements.

Figure 22:
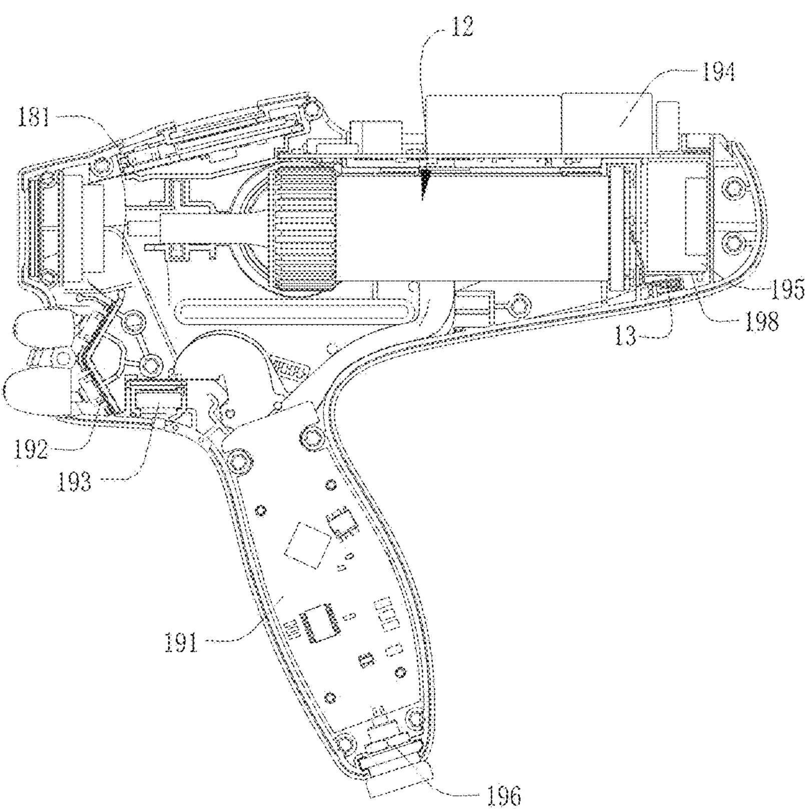
FIG. 22 is a schematic diagram of the layout structure of the internal circuit and the electronic components of the ultrasonic scalpel handle of the present disclosure.

As shown in FIG. 3 and FIG. 22, the ultrasonic scalpel handle 1 is further provided with following components or circuit arrangements: the top of the handle housing 11 is provided with a display screen 181, which is covered by a perspective window to display the information that needs to be indicated, and one side of the display screen 181 is provided with a function key 183; the top of the handle housing 11 is further provided with a PCB group 194, and the rear portion thereof is provided with a transformer 195, which is connected to the elastic conductive member 13 behind the transducer assembly 12 through the power line 198, therefore the wire path is short and the electromagnetic radiation is low. The lower portion of the grip of the handle housing 11 is provided with a connection socket 196 and a protective cover 197, and a connecting wire 31 for detachably connected to the power adapter 3. A circuit board 191 is provided in the grip of the handle housing 11, and the front portion of the grip is further provided with a front key 184, the handle housing 11 is further provided with a loudspeaker 193 and a front key FPC group 192.

The ultrasonic scalpel handle 1 is connected to the power adapter 3, and after the power supply of the power adapter 3 is connected, the front key 184 and the function key 183 are excited to check the system status, and on the excitation of the front key 184, the loudspeaker 193 gives an excitation prompt tone, and the function key 183 is pressed down, at this time, the handle NFC communicates with the cutting tool NFC chip to encode and identify the cutting tool, and to match the output power according to the cutting tool coding, and after the communication matching is completed (after the cutting tool is mounted, a master control chip in the handle successfully shakes hands with the cutting tool NFC chip to establish communication, read various information of the cutting tool in the NFC chip, including but not limited to the product ID, the number of times used, the working power of the cutting tool, the working frequency of the cutting tool, etc., after the information is successfully read and the information is valid, the master control chip in the handle determines that the cutting tool is an effective cutting tool, and considers that the matching program is completed, and it can enter the standby waiting for the excitation work), the system can perform surgical operation. The operator can select a working mode through the function key 183, and the working mode can be viewed on the display screen 181. When the system fails, the loudspeaker 193 will give an alarm prompt tone, and the display screen 181 will prompt a fault code.

When the soft tissue is processed, the front key 184 is excited, and the electricity of the power plate is transmitted to the ceramic sheet of the horn shaft 1222 of the transducer 122 through the control board, the ceramic sheet generates high-frequency ultrasonic vibration, and the ultrasonic vibration is amplified by the horn shaft 1222 and transmitted to the tool bar 25 of the cutting tool 2, to achieve the cutting of the tissue (the upper key of the front key 184 is a high-power key mainly used to cut tissues, and the lower key is a low-power key mainly used for vascular sealing), when the tissue is cut off or the blood vessel is sealed, the excitation of the front key 184 stops, the handgrip 145 is released, and the clamp 23 is reset and opened, to complete the closing and opening cycle. Repeat the above process many times to complete the operation (there are also cases of exciting the front key 184 to cut with the clamp 23 is not closed, which is not separately introduced here).

The embodiments described above are only for illustrating the technical concepts and features of the present disclosure, and are intended to make those skilled in the art being able to understand the present disclosure and thereby implement it, and should not be concluded to limit the protective scope of this disclosure. Any equivalent variations or modifications according to the present disclosure should be covered by the protective scope of the present disclosure.

The invention claimed is:

1. An ultrasonic scalpel handle, comprising a handle housing and a transducer assembly, the handle housing having an accommodating cavity, the transducer assembly disposed in the accommodating cavity, wherein the ultrasonic scalpel handle further comprises a connecting assembly disposed in the accommodating cavity and for connecting to a cutting tool, and wherein the connecting assembly comprises:

- a connector, an axis line of the connector extending in a front-rear direction, the connector having a hollow channel penetrating in the front-rear direction, a circumferential side wall of the connector provided with a plurality of through holes, and all the plurality of through holes distributed at intervals in a circumferential direction and communicated with the hollow channel;
- rolling balls, a number of the rolling balls equal to or less than a number of the plurality of through holes, and the rolling balls radially movably arranged in the plurality of through holes;
- a ball cap, the ball cap sleeved on a front portion of the connector in a manner that can relatively slide in the front-rear direction, a portion of an inner peripheral wall of the ball cap forming a position-limit structure, and another portion of the inner peripheral wall of the ball cap forming a yielding structure, wherein:
  - when the position-limit structure is located at an outer circumferences of the plurality of through holes, the rolling balls are at least partially located in the hollow channel; and
  - when the yielding structure is located at the outer circumferences of the plurality of through holes, the rolling balls are located outside the hollow channel, and wherein the yielding structure is located at a front side of the position-limit structure; and
- a first elastic element, the first elastic element disposed between the connector and the ball cap, the first elastic element providing a force required for the ball cap to move forward with respect to the connector and for driving the ball cap to move forward or backward with respect to the connector so as to position the position-limit structure at the outer circumferences of the plurality of through holes.

2. The ultrasonic scalpel handle according to claim 1, wherein a diameter of the plurality of through holes is tapered from outside to inside in a radial direction of the connector, and a bottom diameter of the plurality of through holes is smaller than a diameter of the rolling balls.

3. The ultrasonic scalpel handle according to claim 1, wherein the ball cap comprises a sliding cylinder portion, a pushing portion and a position-limit cylinder portion successively connected from front to back, an inner diameter of the sliding cylinder portion is larger than that of the position-limit cylinder portion, and the pushing portion is a conical cylinder with a tapered inner diameter from front to back, and

- wherein an inner circumferential wall of the sliding cylinder portion forms the yielding structure, and an inner circumferential wall of the position-limit cylinder portion forms the position-limit structure.

4. The ultrasonic scalpel handle according to claim 3, wherein the connector is provided with a position-limit ring, the position-limit ring is located in the hollow channel, and the position-limit ring is located behind the plurality of through holes.

5. The ultrasonic scalpel handle according to claim 1, wherein the ultrasonic scalpel handle further comprises a driving mechanism for driving the connecting assembly to move forward and backward, and the driving mechanism comprises:

- a slider, the slider slidingly arranged on the handle housing and connected to the connector;
- a second elastic element, the second elastic element providing the force required for the slider to move forward;
- a handgrip, the handgrip rotatably arranged on the handle housing, and at least part of the handgrip located outside the handle housing; and
- a linkage assembly, the linkage assembly arranged between the handgrip and the slider and configured to be used to drive the slider to slide backward and forward when rotating the handgrip.

6. The ultrasonic scalpel handle according to claim 5, wherein the slider is provided with a sleeve section slidably sleeved on the connector, a rear portion of the connector is adjustably provided with an adjusting nut, and a third elastic element is provided between the adjusting nut and the sleeve section to drive the adjusting nut and the sleeve section away from each other in the front-rear direction.

7. The ultrasonic scalpel handle according to claim 1, wherein the transducer assembly is configured to be accommodated in the accommodating cavity in a manner that can rotate about its own axis, the transducer assembly comprises a transducer shell and a transducer, the transducer shell comprises a hollow cavity penetrating in the front-rear direction, and at least a rear portion of the transducer is accommodated in the hollow cavity.

8. The ultrasonic scalpel handle according to claim 7, wherein the transducer assembly further comprises an electric plate provided at a rear portion of the transducer shell, the electric plate is provided with a conductive portion, the transducer is electrically connected to the conductive portion, an elastic conductive element is further provided in the accommodating cavity of the handle housing, the elastic conductive element abuts forward against a rear end face of the electric plate, and when the transducer assembly rotates about its own axis with respect to the handle housing, the elastic conductive element maintains contact with the conductive portion to maintain electric connection.

9. The ultrasonic scalpel handle according to claim 8, wherein the conductive portion comprises a first conductive portion and a second conductive portion insulated from each other, the transducer comprises a first electric lead and a second electric lead, the first electric lead is electrically connected to the first conductive portion, and the second electric lead is electrically connected to the second conductive portion, and wherein the elastic conductive element comprises a first elastic conductive element and a second elastic conductive element disposed independently, the first elastic conductive element abuts against the first conductive portion, and the second elastic conductive element abuts against the second conductive portion.

10. The ultrasonic scalpel handle according to claim 9, wherein the first conductive portion and the second conductive portion are in a shape of a disc or ring having the axis line of the transducer assembly as a rotation center.

11. The ultrasonic scalpel handle according to claim 9, wherein the electric plate comprises a plate body, a first conductive piece and a second conductive piece fixed on the plate body and comprising metal materials, the first conductive piece forms the first conductive portion, the second conductive piece forms the second conductive portion, the first elastic conductive element abuts against a rear side of the first conductive piece, and the second elastic conductive element abuts against a rear side of the second conductive piece.

12. The ultrasonic scalpel handle according to claim 11, wherein the second conductive piece is in a shape of a ring and circumferentially disposed on a circumferential outer side of the first conductive piece, and the first conductive piece and the second conductive piece are disposed at intervals in a radial direction of the electric plate.

13. The ultrasonic scalpel handle according to claim 11, wherein the plate body is provided with a first perforated hole and a second perforated hole penetrating in a thickness direction of the plate body, the first electric lead runs through the first perforated hole and is fixedly connected to the first conductive piece, and the second electric lead runs through the second perforated hole and is fixedly connected to the second conductive piece.

14. The ultrasonic scalpel handle according to claim 9, wherein the first elastic conductive element and the second elastic conductive element are both elastic pieces comprising metal materials, an end portion of the first elastic conductive element and an end portion of the second elastic conductive element are fixedly arranged in the handle housing respectively, the other end portion of the first elastic conductive element presses forward against the first conductive portion, and the other end portion of the second elastic conductive element presses forward against the second conductive portion.

15. The ultrasonic scalpel handle according to claim 8, wherein the ultrasonic scalpel handle further comprises a power connecting wire, an end portion of the power connecting wire is fixedly and electrically connected to the elastic conductive element, and the other end portion of the power connecting wire goes out of the accommodating cavity from a lower portion of the handle housing.

16. The ultrasonic scalpel handle according to claim 7, wherein the ultrasonic scalpel handle further comprises a transducer constraint assembly for limiting a rotation of the transducer assembly, and the transducer constraint assembly is divided into two groups on left and right sides of the transducer assembly.

17. The ultrasonic scalpel handle according to claim 16, wherein each of the two groups into which the transducer constraint assembly is divided comprises a pressing bar extending in the front-rear direction, the pressing bar is rotatably arranged on the handle housing around a central line of rotation extending in an up-down direction, a rear portion of the pressing bar is provided with a pressing and holding portion, a constraint structure is arranged between a inner side of the pressing and holding portion and an outer circumference of the transducer shell to limit the rotation of the transducer shell, the constraint structure has a constraint state and a release state, wherein:

when in the constraint state, the two pressing and holding portions on the left and right sides abut against the outer circumference of the transducer shell respectively; and when in the release state, the two pressing and holding portions are separated from the outer circumference of the transducer shell, and wherein the transducer constraint assembly further comprises an elastic element for driving the pressing bar to rotate so that the pressing and holding portion moves away from the transducer shell.

18. The ultrasonic scalpel handle according to claim 17, wherein the transducer shell is cylindrical, and at least one of the pressing and holding portions is an arc-shaped sheet fitting the outer circumference of the transducer shell.

19. The ultrasonic scalpel handle according to claim 17, wherein the constraint structure comprises a first tooth portion arranged on the outer circumference of the transducer shell and a second tooth portion arranged on the inner side of the pressing and holding portion, and when the constraint structure is in the constraint state, the first tooth portion engages the second tooth portion.

20. The ultrasonic scalpel handle according to claim 17, wherein the constraint structure is a positioning structure arranged between the outer circumference of the transducer shell and an inner surface of the pressing and holding portion and enabling a circumferential positioning of the transducer shell by interaction or wherein the constraint structure is a friction-increasing structure arranged between the outer circumference of the transducer shell and the inner surface of the pressing and holding portion for increasing a friction between the outer circumference of the transducer shell and the inner surface of the pressing and holding portion and limiting the rotation of the transducer shell.

21. The ultrasonic scalpel handle according to claim 17, wherein left and right portions of the transducer shell are provided with two operating windows, an outer side of each of the two operating windows is covered with a rubber configured to elastically deform, and the two pressing and holding portions block the two operating windows from an inner side of the handle housing, respectively.

22. An ultrasonic scalpel, wherein the ultrasonic scalpel comprises the ultrasonic scalpel handle according to claim 1, and further comprises a cutting tool detachably mounted on the ultrasonic scalpel handle, wherein the cutting tool comprises an inner tube, an outer tube and a tool bar which extend in the front-rear direction, wherein the tool bar runs through the inner tube, the outer tube is sleeved outside the inner tube, the tool bar and the outer tube are fixed to each other and are arranged in a manner that can move synchronously with respect to the inner tube forward and backward, the transducer assembly at least comprises a transducer, the transducer comprises a horn shaft which extends in the front-rear direction, the inner tube comprises an inner tube body and a mounting boss extending rearward from a rear end of the inner tube body, an outer diameter of the mounting boss is larger than an outer diameter of the inner tube body, a position-limit surface is formed at a position where the inner tube body is connected to the mounting boss, an outer circumference of the mounting boss is a conical inclined surface with gradually increasing outer diameter from rear to front, the tool bar runs through the hollow channel in a manner that can slide in an axial direction, a rear end portion of the tool bar is fixedly connected with the horn shaft, the rolling balls are embedded in the plurality of through holes in a fitted manner, the rolling balls are at least partially located in the hollow channel, and the position-limit surface is located behind the rolling balls.

23. The ultrasonic scalpel according to claim 22, wherein a rear portion of the tool bar is threaded to a front portion of the horn shaft, the tool bar is disposed coaxially with the horn shaft, and the ultrasonic scalpel handle further comprises a self-tightening assembly arranged on the front portion of the handle housing and used to drive the cutting tool to rotate around its own axis.

24. The ultrasonic scalpel according to claim 23, wherein the self-tightening assembly comprises an outer ring, a rotary knob inner sleeve, and an elastic piece arranged between an outer circumference of the rotary knob inner sleeve and an inner circumference of the outer ring, wherein the inner circumference of the outer ring is provided with a plurality of positioning grooves, each of the plurality of positioning grooves extends in the front-rear direction, an outer periphery of a rear portion of the outer tube is provided with a plurality of ribs at intervals extending in the front-rear direction, and the plurality of ribs fit the plurality of positioning grooves one-to-one correspondingly.

25. An ultrasonic scalpel, comprising an ultrasonic scalpel handle and a cutting tool detachably connected to the ultrasonic scalpel handle, the cutting tool comprising an inner tube, an outer tube and a tool bar which extend in a front-rear direction, wherein the tool bar runs through the inner tube, the outer tube sleeved outside the inner tube, wherein the ultrasonic scalpel handle comprises a handle housing and a transducer assembly, and the transducer assembly at least comprises a transducer, and the transducer comprises a horn shaft which extends in the front-rear direction, wherein the ultrasonic scalpel handle further comprises a connecting assembly, the connecting assembly comprises:

a connector, an axis line of the connector extending in the front-rear direction, the connector having a hollow channel through which the inner tube can slide in from front to rear, a circumferential side wall of the connector provided with a plurality of through holes, and all the plurality of through holes distributed at intervals in a circumferential direction and communicated with the hollow channel;

rolling balls, a number of the rolling balls equal to or less than a number of the plurality of through holes, and the rolling balls arranged in the plurality of through holes;

a ball cap, the ball cap sleeved on a front portion of the connector in a manner that can slide in the front-rear direction, a yielding channel configured to accommodate the rolling balls being formed between a portion of an inner circumferential wall of the ball cap and an outer circumferential wall of the connector, and a position-limit structure configured to limit the rolling balls in the plurality of through holes being formed on another portion of the inner circumferential wall of the ball cap; and a first elastic element, the first elastic element disposed between the connector and the ball cap, and driving the ball cap to move forward, such that the position-limit structure limits the rolling balls in the plurality of through holes, wherein the inner tube comprises an inner tube body and a mounting boss extending rearward from an inner end of the inner tube body, an outer diameter of the mounting boss is larger than an outer diameter of the inner tube body, a position-limit surface is formed at a position where the inner tube body is connected to the mounting boss, an outer circumference of the mounting boss is a conical inclined surface with gradually increasing outer diameter from rear to front, the tool bar runs through the hollow channel in a manner that can slide in an axial direction, a rear end portion of the tool bar is fixedly connected with the horn shaft, the rolling balls are correspondingly embedded in the plurality of through holes in a fitted manner, the rolling balls are at least partially located in the hollow channel, and the position-limit surface is located behind the rolling balls.

26. The ultrasonic scalpel according to claim 25, wherein the connector is provided with a position-limit ring located in the hollow channel, the tool bar relatively slidably runs through the position-limit ring, and the mounting boss of the inner tube is limited between the position-limit ring and the rolling balls in the front-rear direction.

27. The ultrasonic scalpel according to claim 25, wherein the ball cap comprises a sliding cylinder portion, a pushing portion, and a position-limit cylinder portion successively connected from front to back, an inner diameter of the sliding cylinder portion is larger than that of the position-limit cylinder portion, and the pushing portion is a conical cylinder with a tapered inner diameter from front to back, and wherein the yielding channel is formed between the sliding cylinder portion and the connector, and an inner circumferential wall of the position-limit cylinder portion forms the position-limit structure.

28. The ultrasonic scalpel according to claim 25, wherein a diameter of the plurality of through holes is tapered from outside to inside in a radial direction of the connector, and a bottom diameter of the plurality of through holes is smaller than a diameter of the rolling balls.

29. The ultrasonic scalpel according to claim 25, wherein the inner tube is arranged coaxially with the outer tube, the inner tube runs through a tube cavity of the outer tube in a manner that can slide in the axial direction, a cutting tool position-limit structure is provided between the inner tube and the outer tube to limit a relative sliding displacement of the inner tube and the outer tube along the axial direction, and the tool bar is fixed to the outer tube so as to maintain a synchronous movement.

30. The ultrasonic scalpel according to claim 29, wherein the ultrasonic scalpel handle further comprises a driving mechanism for driving the connecting assembly to move forward and backward so as to cause the inner tube to move forward and backward with respect to the outer tube, and the driving mechanism comprises:

a slider, the slider slidingly arranged on the handle housing, and the slider connected to the connector;

a second elastic element, the second elastic element providing a force required for the slider to move forward;

a handgrip, the handgrip rotatably arranged on the handle housing, and at least part of the handgrip located outside the handle housing; and a linkage assembly, the linkage assembly arranged between the handgrip and the slider and configured to drive the slider to slide forward and backward when rotating the handgrip.

31. The ultrasonic scalpel according to claim 30, wherein the slider is provided with a sleeve section slidably sleeved on the connector, a rear portion of the connector is adjustably provided with an adjusting nut, and a third elastic element is provided between the adjusting nut and the sleeve section to drive the adjusting nut and the sleeve section away from each other in the front-rear direction.

32. The ultrasonic scalpel according to claim 29, wherein a rear portion of the cutting tool runs through the hollow channel in a manner that can rotate around its own axis line, a rear portion of the tool bar is threaded to a front portion of the horn shaft, the tool bar is disposed coaxially with the horn shaft, and the ultrasonic scalpel handle further comprises a self-tightening assembly arranged on a front portion of the handle housing and used to drive the cutting tool to rotate around its own axis line.

33. The ultrasonic scalpel according to claim 29, wherein the transducer assembly further comprises a transducer shell, the transducer is fixedly mounted in the transducer shell, the transducer is disposed coaxially with the transducer shell, the transducer assembly is disposed in the handle housing in a manner that can rotate around its own axis line, and wherein the transducer assembly further comprises an electric plate provided at a rear portion of the transducer shell, the electric plate is provided with a conductive portion, the transducer is electrically connected to the conductive portion, an elastic conductive element is further provided in the handle housing, the elastic conductive element abuts forward against a rear end face of the electric plate, and, when the transducer assembly rotates about its own axis with respect to the handle housing, the elastic conductive element is always in contact with the conductive portion to maintain electric connection.

34. An ultrasonic scalpel system, wherein the ultrasonic scalpel system comprises the ultrasonic scalpel according to claim 25 and a power adapter for supplying energy to the ultrasonic scalpel, wherein a connecting wire of the power adapter extends downward from a lower portion of the ultrasonic scalpel handle.

* * * * *